US010188631B2

(12) United States Patent
Agostinetto

(10) Patent No.: US 10,188,631 B2
(45) Date of Patent: Jan. 29, 2019

(54) TOPICAL LIQUID COMPOSITION COMPRISING MELATONIN

(71) Applicant: ARES TRADING S.A., Aubonne (CH)

(72) Inventor: Rita Agostinetto, Rocca di Papa (IT)

(73) Assignee: ARES TRADING S.A., Aubonne (CH)

( * ) Notice: Subject to any disclaimer, the term of this patent is extended or adjusted under 35 U.S.C. 154(b) by 0 days.

(21) Appl. No.: 15/548,315

(22) PCT Filed: Feb. 15, 2016

(86) PCT No.: PCT/EP2016/053197
§ 371 (c)(1),
(2) Date: Aug. 2, 2017

(87) PCT Pub. No.: WO2016/131784
PCT Pub. Date: Aug. 25, 2016

(65) Prior Publication Data
US 2018/0021308 A1 Jan. 25, 2018

(30) Foreign Application Priority Data
Feb. 17, 2015 (EP) .................... 15155389

(51) Int. Cl.
| | | |
|---|---|---|
| A61K 31/405 | (2006.01) | |
| A61K 9/00 | (2006.01) | |
| A61K 31/4045 | (2006.01) | |
| A61K 47/02 | (2006.01) | |
| A61K 47/18 | (2017.01) | |
| A61K 9/08 | (2006.01) | |
| A61K 31/198 | (2006.01) | |
| A61K 47/26 | (2006.01) | |

(52) U.S. Cl.
CPC ........ *A61K 31/4045* (2013.01); *A61K 9/0034* (2013.01); *A61K 9/08* (2013.01); *A61K 31/198* (2013.01); *A61K 47/02* (2013.01); *A61K 47/183* (2013.01); *A61K 47/26* (2013.01)

(58) Field of Classification Search
CPC . A61K 31/454; A61K 9/0034; A61K 31/4045
USPC .......................................... 514/415; 424/400
See application file for complete search history.

(56) References Cited

U.S. PATENT DOCUMENTS

2009/0226879 A1* 9/2009 Ali bin M. Abdullah .................... C12N 5/0604
435/2

FOREIGN PATENT DOCUMENTS

WO 0053176 A1 9/2000
WO 2013178587 A1 12/2013

OTHER PUBLICATIONS

Givens et al. "Diagnostic dilemma encountered when detecting bovine viral diarrhea virus in IVF embryo production," Theriogenology, 2002, vol. 58, pp. 1399-1407.*
Choe et al., "Synergistic Effects of Glutathione and Beta-Mercaptoethanol Treatment During In Vitro Maturation of Porcine Oocytes on Early Embryonic Development in a Culture System Supplemented with L-cysteine," Journal of Reproduction and Development, Jan. 1, 2010, pp. 575-582, vol. 56, No. 6.
Daya et al., "The Effect of Variations in pH and Temperature on Stability of Melatonin in Aqueous Solution," Journal of Pineal Research, Sep. 1, 2001, pp. 155-158, vol. 31, No. 2.
International Search Report and Written Opinion dated Apr. 18, 2016 in International Application No. PCT/EP2016/053197, 10 pages.
March, "Advanced Organic Chemistry: Reactions, Mechanisms, and Structure," Chapter 4: CIS-Trans Isomerism, Jul. 1992, pp. 131-133, Wiley Interscience Publication.
March, "Advanced Organic Chemistry: Reactions, Mechanisms, and Structure," 4th Edition, Chapter 4: Optical Activity and Chirality, Jan. 2001, pp. 94-164, Wiley Interscience Publication.
Deady, "Ring Nitrogen Oxidation of Amino Substituted Nitrogen Heterocycles with m-Chloroperbenzoic Acid," Synthetic Communications, Jul. 1977, pp. 509-514, vol. 7, No. 8.
Bundgaard, "Design of Prodrugs," Elsevier, Nov. 1985, ISBN-10: 044480675X, ISBN-13: 978-04-44806758, title page and table of contents only.
Krogsgaard-Larsen et al., "A Textbook of Drug Design and Development," Chapter 5: Design and Application of Prodrugs, Jul. 1991, pp. 113-191.
Higuchi et al., "Pro-drugs as Novel Drug Delivery Systems," ACS Symposium Series 14, American Chemical Society, Jun. 1975, title page and table of contents only.
Roche, "Bioreversible Carriers in Drug Design: Theory and Application," Pergamon Press, 1987, title page and table of contents only.
Kakeya et al, "Studies on Prodrugs of Cephalosporins. I. Synthesis and Biological Properties of Glycyloxybenzoyloxymethyl and Glycylaminobenzoyloxymethyl Esters of 7 Beta-[2-(2-Aminothiazol-4-yl)-(Z)-2-methoxyiminoacetamido]-3-methyl-3-cephem-4-carboxylic Acid," Chemical and Pharmaceutical Bulletin, 1984, pp. 692-698, vol. 32, No. 2.
Bundgaard, "Means to Enhance Penetration: Prodrugs as a Means to Improve the Delivery of Peptide Drugs," Advanced Drug Delivery Reviews, Jan.-Feb. 1992, pp. 1-38, vol. 8, Issue 1.

(Continued)

*Primary Examiner* — Shengjun Wang
(74) *Attorney, Agent, or Firm* — Carter, DeLuca, Farrell & Schm

(57) ABSTRACT

The present invention relates to a novel melatonin-based formulation, particularly a topical liquid composition of melatonin (or analog thereof) suitable for use in intrauterine washing performed during medically assisted reproduction (e.g. in vitro fertilization—IVF). Melatonin is notoriously unstable, especially in solution. The compositions of the invention exhibit high stability, which allows them to be kept for prolonged periods before their eventual use in the inhibition or prevention of embryonic implantation failure.

15 Claims, No Drawings

(56) References Cited

OTHER PUBLICATIONS

Charton, "Prodrug Lability Prediction through the Use of Substituent Effects," Methods in Enzymology, 1985, pp. 324-340, vol. 112.
Nielsen et al., "Glycolamide Esters as Biolabile Prodrugs of Carboxylic Acid Agents: Synthesis, Stability, Bioconversion, and Physicochemical Properties," Journal of Pharmaceutical Sciences, Apr. 1988, pp. 285-298, vol. 77, No. 4.
Bundgaard, "Formation of Prodrugs of Amines, Amides, Ureides, and Imides," Method in Enzymology, 1985, pp. 347-359, vol. 112.
Fleisher et al., "Design of Prodrugs for Improved Gastrointestinal Absorption by Intestinal Enzyme Targeting," Methods in Enzymology, 1985, pp. 360-381, vol. 112.
Nelson, "Alteration of Drug Metabolism by the Use of Prodrugs," Methods in Enzymology, 1985, pp. 340-347, vol. 112.
Notari, "Theory and Practice of Prodrug Kinetics," Methods in Enzymology, 1985, pp. 309-323, vol. 112.
Bodor, "Targeting of Drugs to the Brain," Methods in Enzymology, 1985, pp. 381-396, vol. 112.

\* cited by examiner

TOPICAL LIQUID COMPOSITION COMPRISING MELATONIN

CROSS REFERENCE TO RELATED APPLICATIONS

This application is a U.S. National Stage entry of International Application No. PCT/EP2016/053197, filed on Feb. 15, 2016, which claims priority to European Patent Application No. 15155389.8, filed on Feb. 17, 2015, the disclosures of each of which are hereby incorporated by reference herein in their entirety.

INTRODUCTION

The present invention relates to a novel melatonin-based formulation, particularly a topical liquid composition of melatonin (or analog thereof), which may be used for intrauterine washing during medically assisted reproduction (e.g. in vitro fertilisation—IVF) to promote embryonic implantation and/or inhibit or prevent failure of embryonic implantation into the uterus. The invention also relates inter alia to specific uses of the novel melatonin formulation, methods of producing the formulation, and medical devices comprising said formulation.

BACKGROUND

Demand for medically assisted reproduction (MAR) continues to increase, in part due to the widening availability of treatments such as in vitro fertilisation (IVF), and also due to the increasing prevalence of fertility issues that act as a barrier to reproduction.

The IVF process involves in vitro fertilisation of one or more pre-obtained eggs (ova) before embryo(s), ultimately formed thereby, are transferred (back) into a uterus to allow embryonic implantation to occur. Typically, the IVF process is preceded by monitoring and stimulation of the ovulatory process before an ovum (or more typically several ova) is removed from the ovaries. The extracted ovum is then contacted with sperm in a fluid medium in a laboratory to facilitate fertilisation. The fertilised ovum (zygote) is then cultured for several days in an appropriate growth medium to form an embryo(s), before the embryo(s) are finally transferred (back) to a uterus. Pregnancy may then be established following successful implantation of the embryo(s) into the uterus.

The success of MAR techniques such as IVF depends on a complex array of factors, some of which can be readily controlled whilst others cannot. Often, multiple embryos (formed via IVF) are transferred to a uterus in order to improve the overall success rate of the IVF treatment, especially where fertility issues are particularly pronounced. In particular, impregnating a uterus with multiple embryos decreases the likelihood of complete embryonic implantation failure, since the probability that at least one of the embryos will become successfully implanted within the uterus is increased. However, such a strategy carries inherant risks, since multiple implantations can lead to multiple pregnancies/multiple births, which affords well known dangers. As such, there have been various advances in the field of medically assisted reproduction to improve implantation rates, not least to reduce multiple embryo transfers and the consequential risks arising therefrom. For example, luteal support is provided via the administration of medication, such as progesterone, progestins or GnRH agonists, to increase the success rate of implantation and early embryogenesis. However, implantation rates are often still too low to completely dispense with multiple embryo transfers.

The implantation of the human embryo into the uterus is a complex mechanism, which involves both the embryo, and the endometrial epithelium. The phases of apposition, adhesion and invasion involves a multiplicity of molecules, which play an unique role in the process, the molecular dialogue between the conceived and the endometrium implies interactions among cells, and between cells and biochemical factors. These mechanisms, if suitably expressed or inhibited, are of help to determine the receptivity or non-receptivity state of the endometrium versus the embryo.

Embryonic implantation and relevant mechanisms are described in some detail in WO 2013/178587 (MAXIA et al), especially page 1, line 6 to page 6, line 17 thereof, which is hereby incorporated by reference.

Despite the advanced state of MAR technologies in the present day, embryonic implantation failure still remains an unsettled problem and is considered a principle reason for infertility in healthy women. Implantation success rates, using MAR, tend to be about 25%. Inadequate uterine receptivity is therefore deemed to be responsible for approximately two thirds of all failures (for one third the embryo is considered as being responsible).

WO 2013/178587 (MAXIA et al), which is hereby incorporated by reference, discloses recent advances stemming from the recognition of melatonin's key role in the embryonic nesting process. MAXIA et al, describes the use of melatonin (and/or analogs thereof) to promote embryonic implantation and/or mitigate against embryonic implantation failure, especially in mammalian subjects suffering from infertility or polyabortion. In particular, MAXIA et al describes melatonin-containing topical uterine washing/endometrial washing compositions which may be advantageously topically administered within the uterus at the time of or after oocyte retrieval, though suitably several days before embryonic transfer to said uterus. Such washings were shown to dramatically improve implantation success rates and consequential pregnancy rates.

However, there remains a need to optimise topical melatonin formulations for MAR treatments, and in particular address formulation stability issues (for all stages of its production, storage, shipping and use) without compromising (or with minimal compromises in respect of) formulation efficacy; clinical safety; manufacturing viability, consistency, cost, and quality control. The development of such optimised formulations is a significant challenge in view of the delicate balance and interplay between the respective components of such formulations. As such, significant research and development was undertaken by the present applicants to develop alternative and/or improved liquid formulations of melatonin. Desirably, any new such formulations would solve at least one problem inherent in the prior art.

SUMMARY OF THE INVENTION

According to a first aspect of the present invention there is provided a topical liquid composition (suitably for intrauterine washing), the composition comprising:

melatonin (N-acetyl-5-methoxytryptamine) and/or an analog thereof, or a pharmaceutically acceptable salt or solvate thereof; and a buffer system;

wherein the composition optionally further comprises one or more components selected from the group including amino acid(s); tonicifier(s); surfactant(s); and sugar(s); wherein the composition optionally further comprises one or more (additional) pharmaceutically acceptable excipient(s), diluents(s) and/or carrier(s).

According to a further aspect of the present invention there is provided a topical liquid composition for intrauterine washing, the composition comprising:

melatonin (N-acetyl-5-methoxytryptamine) or an analog thereof, or a pharmaceutically acceptable salt or solvate thereof;

a buffer system; and a first amino acid comprising at least one sulphur atom.

According to a further aspect of the present invention there is provided a topical liquid composition for intrauterine washing, the composition comprising:

melatonin (N-acetyl-5-methoxytryptamine) or an analog thereof, or a pharmaceutically acceptable salt or solvate thereof;

a buffer system; and a surfactant;

wherein the composition has a pH between 7 and 8.5.

According to a further aspect of the present invention there is provided a method of manufacturing a topical liquid composition, the method comprising mixing together (or otherwise forming a mixture of):

melatonin (N-acetyl-5-methoxytryptamine) and/or an analog thereof, or a pharmaceutically acceptable salt or solvate thereof; and a buffer system;

optionally one or more components selected from the group including amino acid(s); tonicifier(s); surfactant(s); and sugar(s); and/or optionally one or more (additional) pharmaceutically acceptable excipient(s), diluents(s) and/or carrier(s).

optionally in any amount, concentration, or form stipulated; and optionally adjusting any one or more parameters given herein in relation to a topical liquid composition (e.g. pH, osmolality).

According to a further aspect of the present invention there is provided a topical liquid composition obtainable by, obtained by, or directly obtained by a method of manufacturing a topical liquid composition as defined herein.

According to a further aspect of the present invention there is provided a topical liquid composition as defined herein for use in therapy.

According to a further aspect of the present invention there is provided a topical liquid composition as defined herein for use in the treatment of infertility.

According to a further aspect of the present invention there is provided a topical liquid composition (suitably for intrauterine washing) as defined herein for use in assisted reproduction.

According to a further aspect of the present invention there is provided a topical liquid composition as defined herein for use in in vitro fertilisation treatment.

According to a further aspect of the present invention there is provided a topical liquid composition as defined herein for use in the treatment of embryonic implantation failure (especially during assisted reproduction treatments).

According to a further aspect of the present invention there is provided a topical liquid composition as defined herein for use in promoting embryonic implantation, improving embryonic implantation, inhibiting and/or preventing embryonic implantation failure, reducing the probability of embryonic implantation failure, facilitating assisted reproduction, promoting uterine receptivity to embryonic implantation, and/or treating a uterus.

According to a further aspect of the present invention there is provided a package or medical device, comprising a sterile container pre-filled or configured for filling with a topical liquid composition as defined herein.

According to a further aspect of the present invention there is provided a kit of parts comprising a package or medical device as defined herein, a topical liquid composition as defined herein (optionally contained in the package or medical device), and optionally a set of instructions with directions regarding the administration (e.g. topical) of the topical liquid composition.

According to a further aspect of the present invention there is provided a method of manufacturing a package or a medical device, the method comprising incorporating a topical liquid composition as defined herein within a package or medical device.

According to an eleventh aspect of the present invention there is provided a package or medical device obtainable by, obtained by, or directly obtained by a method of manufacturing a package or a medical device as defined herein.

According to a further aspect of the present invention there is provided a method of treating a disease, condition or medical disorder in a patient in need of such treatment, said method comprising administering to said patient a therapeutically effective amount of a topical liquid composition as defined herein.

According to a further aspect of the present invention there is provided a use of a topical liquid composition as defined herein in the preparation of a uterus for fertility treatment.

According to a further aspect of the present invention there is provided a use of a topical liquid composition as defined herein in the manufacture of a medicament for the treatment of a disease, condition or disorder.

According to a further aspect of the present invention there is provided a method of treating infertility in a patient in need of such treatment, said method comprising administering to said patient a therapeutically effective amount of a topical liquid composition as defined herein.

According to a further aspect of the present invention there is provided a use of a topical liquid composition as defined herein in infertility treatment.

According to a seventeenth aspect of the present invention there is provided a use of a topical liquid composition as defined herein in the manufacture of a medicament for the treatment of infertility.

According to a further aspect of the present invention there is provided a method of treating embryonic implantation failure in a patient in need of such treatment, said method comprising administering to said patient a therapeutically effective amount of a topical liquid composition as defined herein.

According to a further aspect of the present invention there is provided a use of a topical liquid composition as defined herein for treating infertility failure.

According to a seventeenth aspect of the present invention there is provided a use of a topical liquid composition as defined herein in the manufacture of a medicament for the treatment of embryonic implantation failure.

According to a further aspect of the present invention there is provided a method of promoting embryonic implantation, a method of improving embryonic implantation, a method of inhibiting and/or preventing embryonic implantation failure, a method of reducing the probability of embryonic implantation failure, a method of facilitating assisted reproduction, a method of promoting uterine receptivity to embryonic implantation, and/or a method of treating a uterus, in a patient in need of such treatment, said method comprising administering to said patient a therapeutically effective amount of a topical liquid composition as defined herein.

According to a further aspect of the present invention there is provided a use of a topical liquid composition as defined herein for promoting embryonic implantation, improving embryonic implantation, inhibiting and/or preventing embryonic implantation failure, reducing the probability of embryonic implantation failure, facilitating assisted reproduction, promoting uterine receptivity to embryonic implantation, and/or treating a uterus.

According to a further aspect of the present invention there is provided a use of a topical liquid composition as defined herein in the manufacture of a medicament for promoting embryonic implantation, improving embryonic implantation, inhibiting and/or preventing embryonic implantation failure, reducing the probability of embryonic implantation failure, facilitating assisted reproduction, promoting uterine receptivity to embryonic implantation, and/or treating a uterus.

According to a further aspect of the present invention there is provided a method of washing and/or irrigating a uterus and/or endometrium, the method comprising topically administering a topical liquid composition as defined herein to the uterus and/or endometrium.

According to a further aspect of the present invention there is provided a method of facilitating the implantation of an embryo within a uterus, the method comprising:
 (i) washing and/or irrigating the uterus and/or endometrium with a topical liquid composition as defined herein;
 (ii) transferring an embryo (e.g. one form via IVF) to the uterus (suitably after, suitably one or more days after, step (i)); and
 (iii) allowing the embryo to become implanted within the uterus (and optionally monitoring the progress of implantation and/or pregnancy thereafter).

In further aspects, the invention provides a topical liquid composition, a package or medical device, a kit of parts, a method of manufacturing a topical liquid composition, a method of manufacturing a package or medical device, a method of treating, a topical liquid composition for use, and a use of a topical liquid composition in the manufacture of a medicament, essentially as defined herein (including in any of the aforementioned aspects) except that, rather than being specific to "melatonin" (and analogs thereof), the invention may instead apply (and thereby be defined as relating) to any active which promotes embryonic implantation or otherwise inhibits/prevents embryonic implantation failure in assisted reproduction (especially when used as an intrauterine washing composition). The relevant active is suitably one which has received FDA approval. As such, any reference herein to "melatonin" may, unless incompatible therewith, be construed as a reference to any active for the purpose of these additional aspects of the invention (whether this relates to absolute or relative amounts, concentrations, parameters, or properties).

Suitably, the compositions, packages, and medical devices defined herein are for use in assisted reproduction, in particular in the inhibition and/or prevention of embryonic implantation failure into the uterus. Such compositions, packages, and medical devices are suitably for use in the medical or veterinary field. Suitably such compositions, packages, and medical devices are for topical administration, suitably into the uterus. The compositions, packages, and medical devices are suitably for use in assisting reproduction in a mammalian subject (suitably a female mammalian subject), suitably in a subject in need of such treatment, most suitably for use in assisting reproduction in a human subject. Suitably, topical administration of the compositions, packages, and medical devices involves topical administration of an (therapeutically) effective amount of the composition.

Any features, including optional, suitable, and preferred features, described in relation to any particular aspect of the invention may also be features, including optional, suitable and preferred features, of any other aspect of the present invention.

DETAILED DESCRIPTION OF THE INVENTION

Definitions

Unless otherwise stated, the following terms used in the specification and claims have the following meanings set out below.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

For the avoidance of doubt, it is hereby stated that the information disclosed earlier in this specification under the heading "Background" is relevant to the invention and is to be read as part of the disclosure of the invention.

Suitably, unless stated otherwise, where reference is made to a parameter (e.g. pH, pKa, etc.) or state of a material (e.g. liquid, gas, etc.) which may depend on pressure and/or temperature, suitably in the absence of further clarification such a reference refers to said parameter at standard ambient temperature and pressure (SATP). SATP is a temperature of 298.15 K (25° C., 77° F.) and an absolute pressure of 100 kPa (14.504 psi, 0.987 atm).

Unless stated otherwise, any reference herein to an "average" value is intended to relate to the mean value.

Herein, the term "buffer" or "buffer solution" refers to a generally aqueous solution comprising a mixture of an acid (usually a weak acid, e.g. phosphoric acid or one or more hydrogenphosphate species) and its conjugate base (e.g. a phosphate, for example, sodium phosphate or derivatives thereof) or alternatively a mixture of a base (usually a weak base, e.g. histidine) and its conjugate acid (e.g. protonated histidine salt). The pH of a "buffer solution" will change very only slightly upon addition of a small quantity of strong acid or base due to the "buffering effect" imparted by the "buffering agent".

Herein, a "buffer system" comprises one or more buffering agent(s) and/or an acid/base conjugate(s) thereof, and more suitably comprises one or more buffering agent(s) and an acid/base conjugate(s) thereof. Unless stated otherwise, any concentrations stipulated herein in relation to a "buffer system" (i.e. a buffer concentration) suitably refers to the combined concentration of the buffering agent(s) and/or acid/base conjugate(s) thereof. In other words, concentrations stipulated herein in relation to a "buffer system" suitably refer to the combined concentration of all the relevant buffering species (i.e. the species in dynamic equilibrium with one another, e.g. phosphate(s)/phosphoric acid(s)). As such, a given concentration of a phosphate and/or a histidine buffer system generally relates to the combined concentration of histidine and the imidazolium form of histidine and/or phosphate(s) and/or phosphoric acid(s). In the case of phosphate buffer systems, such concentrations are usually straightforward to calculate by reference to the input quantities of phosphate salts (including any hydrogen phosphate salts, e.g. monohydrogen phosphate, dihydrogen phosphate, and/or trihydrogen phosphate). In the case of histidine, such concentrations are usually straightforward to calculate by reference to the input quantities of histidine or a salt thereof. The overall pH of the composition comprising the relevant buffer system is generally a reflection of the equilibrium concentration of each of the relevant buffering species (i.e. the balance of buffering agent(s) to acid/base conjugate(s) thereof).

Herein, the term "buffering agent" refers to an acid or base component (usually a weak acid or weak base) of a buffer or buffer solution. A buffering agent helps maintain the pH of a given solution at or near to a pre-determined value, and the buffering agents are generally chosen to complement the pre-determined value. A buffering agent is suitably a single compound which gives rise to a desired buffering effect, especially when said buffering agent is mixed with (and suitably capable of proton exchange with) an appropriate amount (depending on the pre-determined pH desired) of its corresponding "acid/base conjugate", or if the required amount of its corresponding "acid/base conjugate" is formed in situ—this may be achieved by adding strong acid or base until the required pH is reached. By way of example:

A phosphate "buffering agent" is suitably a phosphate salt, for example, a sodium phosphate (which may include one or a mixture of two or more phosphates, such as a mixture of monosodium phosphate, disodium phosphate monobasic, and/or trisodium phosphate) suitably mixed with its acid/base conjugate, phosphoric acid. Such a buffer system may be formed by simply mixing a given amount of phosphate salt(s) with a given amount of phosphoric acid. Alternatively, however, such a buffer may be formed by adding a given amount of a base, suitably a strong base (e.g. sodium hydroxide) to the phosphoric acid until the desired pH (and thus the desired balance of sodium acetate/acetic acid) is reached. Herein, except where the contrary is stated, any concentrations given in relation to a phosphate buffer or phosphate buffering agent suitably refer to the combined concentration of the buffering agent(s) (e.g. sodium phosphate(s)) and/or acid/base conjugate(s) thereof (e.g. phosphoric acid). The skilled person is readily able to calculate such concentrations. Such concentrations may be calculated by reference to the combined concentrations of buffering agent(s) and acid/base conjugate(s), where a buffer system is formed by simply mixing together buffering agent(s) and acid/base conjugate(s). Alternatively, where a buffer system is formed by mixing either the buffering agent(s) or acid/base conjugate(s) with a pH adjuster (e.g. strong acid or strong base) to produce a mixture of each, suitably such concentrations may be calculated by reference to the starting amounts/concentrations of the buffering agent(s) or acid/base conjugate(s) respectively. For example, where a buffer system is formed using a known amount/concentration of phosphoric acid which is mixed with a pH adjuster (e.g. sodium hydroxide) until the desired pH is reached, the concentration of the buffer system may be calculated by reference to the initial amount of phosphoric acid.

A histidine "buffering agent" is the free amino acid, histidine. Since amino acids such as histidine are amphoteric, and thus capable of behaving as both an acid and base, the "buffering agent" is simply the amphoteric compound itself (suitably in zwitterionic form). However, a histidine buffer system or buffer solution may optionally have, added thereto in addition to histidine, a quantity of acid (suitably a strong acid, such as hydrochloric acid) or base (suitably a strong base, such as sodium hydroxide) until the desired pH is reached. As such, some of the histidine present may exhibit a different protonation state than the zwitterionic amino acid. Herein, except where the contrary is stated, any concentrations given in relation to a histidine buffer system suitably refer to the combined concentration of the buffering agent (e.g. histidine) and/or acid/base conjugate(s) thereof (e.g. imidazolium form of histidine). The skilled person is readily able to calculate such concentrations, and may do so by simple reference to the input quantities of histidine or its acid/base conjugate (e.g. histidine hydrochloride). Such concentrations may be calculated by reference to the combined concentrations of buffering agent(s) and acid/base conjugate(s), where a buffer system is formed by simply mixing together buffering agent(s) and acid/base conjugate(s). Alternatively, where a buffer system is formed by mixing either the buffering agent(s) or acid/base conjugate(s) with a pH adjuster (e.g. strong acid or strong base) to produce a mixture of each, suitably such concentrations may be calculated by reference to the starting amounts/concentrations of the buffering agent(s) or acid/base conjugate(s) respectively. For example, where a buffer system is formed using a known amount/concentration of histidine which is mixed with a pH adjuster (e.g. sodium hydroxide) until the desired pH is reached, the concentration of the buffer system may be calculated by reference to the initial amount of histidine. Likewise, the same applies where a buffer system is formed using a known amount/ concentration of histidine imidazolium salt (e.g. histidine hydrochloride) mixed with a pH adjuster (e.g. sodium hydroxide) until the desired pH is reached—in this case the concentration of the buffer system may be calculated by reference to the initial amount of histidine imidazolium salt.

Herein, an "acid/base conjugate" refers to the conjugate acid or conjugate base (whichever is relevant at a particular pH—typically the conjugate acid in the context of the present invention) of a particular "buffering agent". The acid/base conjugate of a phosphate buffering agent (e.g. sodium phosphate) is suitably phosphoric acid (though this may suitably include higher hydrogen phosphate salts, such as mono- or dihydrogen phosphates, which are potentially conjugate acids to phosphate or lower hydrogen phosphate salts thereof). The acid/base conjugate of a histidine buffering agent (e.g. histidine) is suitably the imidazolium form of histidine, suitably an imidazolium salt of histidine. The imidazolium form of histidine may be referred to herein as "imidazolium-histidine", and has the structure:

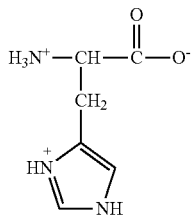

An imidazolium salt of histidine may be referred to as histidine-imidazolium salt, and has essentially the same structure as shown above save for an associated counteraction.

Herein, the term "buffering species" refers to the particular species (excluding any associated counteranions or countercations—i.e. ignore sodium counterions for phosphate(s)/phosphoric acid(s) systems, and ignore chloride or hydroxide counter-ions for histidine/imidazolium-histidine systems) of a given buffer system which are in dynamic equilibrium with (and proton-exchange with) one another. For example, phosphate, monohydrogenphosphate, and dihydrogenphosphate anions and phosphoric acid may together constitute "phosphate buffering species" of a "phosphate buffer system" (though depending on the pH, some may be more prevalent than others within the buffer system). Alternatively and/or additionally, histidine and imidazolium-histidine may together constitute "histidine buffering species" of a "histidine buffer system".

Since it is often somewhat difficult to define quantities (whether absolute or relative) of a buffer system by reference to weight (since the total weight will depend on the desired pH, which will affect the amount of counterions present), herein weight-based quantities may instead be determined by reference to a theoretical weight of a relevant or arbitrary "buffering species". At least two species are generally present in any given set of "buffering species" (in relative amounts that can only be determined by reference to the pH), each with a different molecular weight (which usually differs by just 1, though for phosphate buffers multiple phosphate species may be present). Therefore, to enable viable weight calculations and references, for the purposes of this specification the weight of any given set of "buffering species" is given as a theoretical weight based on just one of the buffering species. Depending on the buffer system in question, this may conveniently be the most acidic of the buffering species (i.e. the most protonated form at any given pH) or the most basic of the buffering species (i.e. the least protonated form at any given pH), or may simply be one of the buffering species. By way of example, in a phosphate system the phosphate buffering species may consist of phosphate anions (ignore countercations) and phosphoric acid (and/or one or more corresponding hydrogenphosphates). The weight of the "buffering species" may therefore be calculated as if phosphoric acid was the only species present in the buffer system (even though phosphate species are clearly present alongside phosphoric acid, and even if only minimal phosphoric acid is actually present at the given pH). Thus, any reference to a weight or weight ratio involving a "phosphatebuffering species" suitably refers to the theoretical weight of phosphoric acid equivalents within the buffer system. As such, where a composition is formed by adding a pH adjuster (e.g. sodium hydroxide) to a fixed amount of phosphoric acid, the original weight of phosphoric acid may be considered to be the weight of the "buffering species" regardless of the ultimate pH. Alternatively, if the concentration (i.e. molarity) of a buffer system is known (or if the relevant buffering system is formed by adding an acidic pH adjust, such as phosphoric acid, to a fixed amount of phosphate species), this can be converted into a weight of "buffering species" by reference to the molecular weight of the most acidic form of the relevant buffering species (e.g. phosphoric acid), and ignoring the fact that phosphate anions are also present. By way of an alternative example, in a histidine buffer system the histidine buffering species may consist of histidine and imidazolium-histidine cations. The weight of the "buffering species" is therefore calculated as if histidine was the only species present in the buffer system (even if imidiazolium-histidine is present alongside histidine). Thus, any reference to a weight or weight ratio involving a "histidine buffering species" suitably refers to the theoretical weight of histidine equivalents within the buffer system. As such, where a composition is formed by adding a pH adjuster (e.g. sodium hydroxide) to a fixed amount of imidazolium histidine, or indeed to a fixed amount of histidine (which may suitably form some imidazolium-histidine upon dissolution in the diluent), the original weight of histidine may be considered to be the weight of the "buffering species" regardless of the ultimate pH. Alternatively, if the concentration (i.e. molarity) of a buffer system is known, this can be converted into a weight of "buffering species" by reference to the molecular weight of the most basic form of the relevant buffering species (e.g. histidine), and ignoring the fact that imidazolium-histidine cations are also present.

It will be understood by those skilled in the art that many buffering species may adopt a variety of different forms. Furthermore, acids, such as phosphoric acid, may in themselves adopt a variety of forms—collectively "phosphoric acids"—and the present invention suitably includes any of these forms.

Unless stated otherwise, references herein to an "amino acid" or "amino acids", whether specific (e.g. methionine, arginine, histidine) or general (e.g. any amino acid), in the context of their presence or otherwise within compositions (especially topical liquid compositions of the invention) relate to the corresponding free amino acid(s) (regardless of its/their protonation state and/or salt form, all of which may be included by a single reference to "amino acid(s)", whether specific or general, though for consistency amounts are suitably calculated by reference to the free amino acid per se). This may suitably include natural and/or artificial amino acids. Unless stated to the contrary, such references are not intended to relate to amino acid residue(s) covalently incorporated as part of a larger compound (as opposed to a composition comprising multiple compounds), such as a peptide or protein (where such amino acid residues are linked via peptide bonds). By way of example, a composition defined as being "free of arginine" does not contain any free arginine (or free arginine salts, such as arginine hydrochloride) but it may still include one or more proteins which do themselves comprise arginine residues. A composition defined as comprising "methionine" contains free methionine (or a salt thereof), regardless of whether or not one or more proteins are present which themselves comprise methionine residues within their overall structure.

Unless stated otherwise, references herein to any one or more "amino acids", whether specific or general, suitably relate to the L-stereoisomers or a racemate thereof, most suitably L-amino acids.

The term "substantially free", when used in relation to a given component of a composition (e.g. "a topical liquid composition substantially free of arginine"), refers to a composition to which essentially none of said component has been added. As explained above, such references have no bearing on the presence of amino acid residue(s) within a protein structure. When a composition is "substantially free" of a given component, said composition suitably comprises no more than 0.001 wt % of said component, suitably no more than 0.0001 wt % of said component, suitably no more than 0.00001 wt %, suitably no more than 0.000001 wt %, suitably no more than 0.0000001 wt % thereof, most suitably no more than 0.0001 parts per billion (by weight).

The term "entirely free", when used in relation to a given component of a composition (e.g. "a topical liquid composition substantially free of arginine"), refers to a composition containing none of said component. As explained above, such references have no bearing on the presence of amino acid residue(s) within a protein structure.

Herein, in the context of the present specification, a "strong acid" is suitably one having a $pK_a$ of −1.0 or less, whereas a "weak acid" is suitably one having a $pK_a$ of 2.0 or more. Herein, in the context of the present specification, a "strong base" is suitably one whose conjugate acid has a $pK_a$ of 12 or higher (suitably 14 or higher), whereas a "weak base" is suitably one whose conjugate acid has a $pK_a$ of 10 or less.

Unless stated otherwise, references herein to a "pKa" should be construed as a pKa value in water at standard ambient temperature and pressure (SATP), suitably of the conjugate acid of the relevant species.

Herein, a "non-reducing sugar" is generally a sugar without any aldehyde moieties or without the capability of forming an aldehyde moiety (e.g. through isomerism).

Herein, a "tonicity modifier" or "tonicifier" refers to a reagent whose inclusion within a composition suitably contributes to (or increases) the overall osmolality and osmolarity of the composition. Suitably, a tonicifier, as used herein includes an agent which functions to render a solution similar in osmotic characteristics to physiologic fluids.

Herein, references to specific amounts of a given component of a composition, especially a buffering agent, amino acid, surfactant, or tonicifier, suitably relate to the amounts of the pure anhydrous form of the relevant component (or compositions formed by using said amounts of the pure anhydrous form), even though such a component may be used in a non-anhydrous form when forming the composition. Amounts of any corresponding non-anhydrous forms (e.g. monohydrates, dihydrates, etc.) may be readily calculated by simply using the appropriate multiplier. The skilled person would readily understand how to judiciously adjust the quantity of diluent/water depending on the form of the components used, in order to derive the target concentrations.

Herein, the term "topical composition" refers to a formulation of an active (i.e. melatonin and/or an analog thereof) which renders the biological activity of the active ingredient therapeutically effective, but which does not include other ingredients which are obviously toxic to a subject to which the formulation are intended to be administered. Suitably the topical composition is technically a pharmaceutical composition (albeit suitably for topical administration) comprising melatonin and/or an analog thereof or a pharmaceutically acceptable salt or solvate thereof. Suitably the composition, and all component parts thereof, are pharmaceutically acceptable.

Herein, the term "stable" generally refers to the physical stability and/or chemical stability and/or biological stability of a component, typically an active or composition thereof, during preservation/storage.

It is to be appreciated that references to "treating" or "treatment" include prophylaxis as well as the alleviation of established symptoms of a condition (where, in the context of the present invention, the condition is suitably "implantation failure"). "Treating" or "treatment" of a state, disorder or condition therefore includes: (1) preventing or delaying the appearance of clinical symptoms of the state, disorder or condition developing in a human or mammal that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the condition or a relapse thereof (in case of maintenance treatment) or at least one clinical or subclinical symptom thereof, or (3) relieving or attenuating the condition, i.e., causing regression of the state, disorder or condition or at least one of its clinical or subclinical symptoms. In particular, treatments of the present invention suitably involve topical administration of the topical liquid compositions defined herein, suitably to and within a uterus of a mammal in need of such treatment. The condition being treated is suitably embryonic implantation failure during assisted reproduction. As such, any methods of treatment defined herein (or corresponding medical uses of compositions defined herein) may be methods of promoting embryonic implantation, methods of improving embryonic implantation, methods of inhibiting and/or preventing embryonic implantation failure, methods of reducing the probability of embryonic implantation failure, methods of facilitating assisted reproduction, a method of promoting uterine receptivity to embryonic implantation, a method of treating a uterus to achieve any of the aforementioned. However, the method of treatment may be simply a method of treating infertility or method of assisted reproduction.

In the context of the present invention, a "therapeutically effective amount" or "effective amount" of the composition (or active thereof) means an amount that is effective, when administered to a mammal for treating a condition, in prophylactic and therapeutic aspect and the composition (or active thereof) is effective in treatment of the diseases concerned.

The "therapeutically effective amount" will vary depending on the compound, the condition and its severity and the age, weight, etc., of the mammal to be treated.

Herein, amounts stipulated for components and ingredients, whether specified in terms of "parts", ppm (parts per million), percentages (%, e.g. wt %), or ratios, are intended to be by weight, unless stated otherwise.

Where the quantity or concentration of a particular component of a given composition is specified as a weight percentage (wt % or % w/w), said weight percentage refers to the percentage of said component by weight relative to the total weight of the composition as a whole. It will be understood by those skilled in the art that the sum of weight percentages of all components of a composition (whether or not specified) will total 100 wt %. However, where not all components are listed (e.g. where compositions are said to "comprise" one or more particular components), the weight percentage balance may optionally be made up to 100 wt % by unspecified ingredients (e.g. a diluent, such as water, or other non-essentially but suitable additives).

Herein, unless stated otherwise, the term "parts" (e.g. parts by weight, pbw) when used in relation to multiple ingredients/components, refers to relative ratios between said multiple ingredients/components. Expressing molar or weight ratios of two, three or more components gives rise to the same effect (e.g. a molar ratio of x, y, and z is $x_1:y_1:z_1$ respectively, or a range $x_1-x_2:y_1-y_2:z_1-z_2$). Though in many embodiments the amounts of individual components within a composition may be given as a "wt %" value, in alternative embodiments any or all such wt % values may be converted to parts by weight (or relative ratios) to define a multi-component composition. This is so because the relative ratios between components is often more important than the absolute concentrations thereof in the topical liquid compositions of the invention. Where a composition comprising multiple ingredients is described in terms of parts by weight alone (i.e. to indicate only relative ratios of ingredients), it is not necessary to stipulate the absolute amounts or concentrations of said ingredients (whether in toto or individually) because the advantages of the invention can stem from the relative ratios of the respective ingredients rather than their absolute quantities or concentrations. However, in certain embodiments, such compositions consist essentially of or consist of the stipulated ingredients and a diluent (e.g. water).

Herein, wherever a composition is defined in terms of absolute weight amounts, weight concentrations, or ranges thereof (e.g. x-y wt % or a concentration in x-y wt/vol, such as x-y mg/mL) of a plurality of individual components, this may be termed an absolute composition. Whenever an absolute composition is defined herein, it gives rise to a corresponding alternative embodiment of a composition (i.e. which may be termed a relative composition) comprising exactly the same plurality of individual components but with their respective amounts, concentrations, or ranges thereof given in parts by weight rather than by absolute weight amounts and concentrations) (e.g. x-y parts by weight or pbw). Such a relative composition suitably defines relative amounts or concentrations of the respective individual components rather than absolute amounts or concentrations. However, where an absolute composition includes a particular component whose amount or concentration is defined by reference to something other than weight (e.g. molar amounts or molar concentration, which is normally stated in relation to a buffer), suitably the corresponding relative composition comprises that particular component but its amount and/or concentration is either not given, is given as the same absolute amount and/or concentration as stipulated in relation to the absolute composition, or (where possible) its amount and/or concentration may be converted into and given in parts by whichever measurement was originally used (e.g. parts by moles). Suitably, the amount and/or concentration of that particular ingredient is either not given or is stipulated as the same absolute amount and/or concentration as stipulated in relation to the corresponding absolute composition. By way of example, an "absolute composition" comprising:

2-200 ng/mL melatonin (N-acetyl-5-methoxytryptamine) and/or an analog thereof, or a pharmaceutically acceptable salt or solvate thereof; and
0.01-100 mM phosphate buffer system;
1-100 mg/mL tonicifier;
water (suitably as the remaining balance by weight);
wherein the pH of the composition is pH 7-8.5;
may alternatively be defined as a "relative composition" comprising:
2-200 parts by weight melatonin (N-acetyl-5-methoxytryptamine) and/or an analog thereof, or a pharmaceutically acceptable salt or solvate thereof; and
(optionally 0.01-100 mM) phosphate buffer system;
1,000,000-100,000,000 parts by weight tonicifier;
water (suitably as the remaining balance by weight);
wherein the pH of the composition is pH 7-8.5.

However, since the absolute composition stated above may have the phosphate buffer system given as an absolute weight concentration (in terms of phosphoric acid equivalents), as follows:

2-200 ng/mL melatonin (N-acetyl-5-methoxytryptamine) and/or an analog thereof, or a pharmaceutically acceptable salt or solvate thereof; and
0.01-100 mM phosphate buffer system (0.098-9.8 mg/mL phosphoric acid equivalents);
1-100 mg/mL tonicifier;
water (suitably as the remaining balance by weight);
wherein the pH of the composition is pH 7-8.5;
a corresponding relative composition may be given as
2-200 parts by weight melatonin (N-acetyl-5-methoxytryptamine) and/or an analog thereof, or a pharmaceutically acceptable salt or solvate thereof; and
98,000-9,800,000 phosphate buffer system (in terms of phosphoric acid equivalents);
1,000,000-100,000,000 parts by weight tonicifier;
water (suitably as the remaining balance by weight);
wherein the pH of the composition is pH 7-8.5.

All relative compositions are thus disclosed by virtue of absolute compositions.

Where a composition is said to comprise a plurality of stipulated ingredients (optionally in stipulated amounts of concentrations), said composition may optionally include additional ingredients other than those stipulated. However, in certain embodiments, a composition said to comprise a plurality of stipulated ingredients may in fact consist essentially of or consist of all the stipulated ingredients.

Herein, where a composition is said to "consists essentially of" a particular component, said composition suitably comprises at least 85 wt % of said component, suitably at least 90 wt % thereof, suitably at least 95 wt % thereof, most suitably at least 99 wt % thereof. Suitably, a composition said to "consist essentially of" a particular component consists of said component save for one or more trace impurities.

Herein, the term "particle size" or "pore size" refers respectively to the length of the longest dimension of a given particle or pore. Both sizes may be measured using a laser particle size analyser and/or electron microscopes (e.g. tunneling electron microscope, TEM, or scanning electron microscope, SEM). The particle count (for any given size)

can be obtained using the protocols and equipment outlined in the Examples, which relates to the particle count of sub-visible particles.

Herein, unless stated otherwise, all chemical nomenclature may be defined in accordance with IUPAC definitions.

Herein, the term "hydrocarbon" is well understood in the art, and refers to compounds containing carbon and hydrogen only. The term "hydrocarbyl" general refers any aliphatic, acyclic, or cyclic (including aryl) hydrocarbon group, suitably with no heteroatoms. Such compounds include, inter alia, alkanes, alkenes, alkynes, arenes, and cyclic versions thereof. The term "hydrocarbon" anthracene, naphthalene, benzene, and/or derivatives thereof (e.g. toluene).

Herein, the term "carbocyclyl", "carbocycle" or "carbocyclic" refers to a radical of a non-aromatic cyclic hydrocarbon group, generally having from 3 to 10 ring carbon atoms (i.e. (3-10C)carbocyclyl) and zero heteroatoms in the non-aromatic ring system. Suitably, carbocyclyl groups include (3-nC)cycloalkyl and (3-nC)cycloalkenyl. Exemplary embodiments include: cyclobutyl, cyclobutenyl, cyclopentyl, cyclopentenyl, cyclohexyl, cyclohexenyl, cyclohexadienyl, cycloheptyl, cycloheptenyl, cycloheptadienyl, cycloheptatrienyl, cyclooctyl, cyclooctenyl, bicyclo[2.2.1]heptanyl, bicyclo[2.2.2]octanyl, and the like.

Herein, the term "macrocyclyl", "macrocycle" or "macrocyclic" refers to macrocyclic rings, which are well known in the art. Such macrocyicic rings are suitably cyclic macromolecules or a macromolecular cyclic portions of a molecule. Suitably a macrocyclic ring has nine or more atoms within the ring. Suitably a macrocyclic ring has three or more internal electron-pair donating atoms. A macrocyclic ring is suitably a cyclic molecule able to co-ordinate to a central metal species (e.g. $Mg^{2+}$). Examples include porphyrins.

Herein, the term "carbohydrate" is well understood in the art, and refers to compounds containing carbon, hydrogen, and oxygen only. Such compounds include esters, ketones, aldehydes, sugars, etc.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

An "alkylene," "alkenylene," or "alkynylene" group is an alkyl, alkenyl, or alkynyl group that is positioned between and serves to connect two other chemical groups. Thus, "(1-6C)alkylene" means a linear saturated divalent hydrocarbon radical of one to six carbon atoms or a branched saturated divalent hydrocarbon radical of three to six carbon atoms, for example, methylene, ethylene, propylene, 2-methylpropylene, pentylene, and the like.

"(2-6C)alkenylene" means a linear divalent hydrocarbon radical of two to six carbon atoms or a branched divalent hydrocarbon radical of three to six carbon atoms, containing at least one double bond, for example, as in ethenylene, 2,4-pentadienylene, and the like.

"(2-6C)alkynylene" means a linear divalent hydrocarbon radical of two to six carbon atoms or a branched divalent hydrocarbon radical of three to six carbon atoms, containing at least one triple bond, for example, as in ethynylene, propynylene, and butynylene and the like.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicyclo[2.2.1]heptyl.

"(3-8C)cycloalkenyl" means a hydrocarbon ring containing at least one double bond, for example, cyclobutenyl, cyclopentenyl, cyclohexenyl or cycloheptenyl, such as 3-cyclohexen-1-yl, or cyclooctenyl.

"(3-8C)cycloalkyl-(1-6C)alkylene" means a (3-8C)cycloalkyl group covalently attached to a (1-6C)alkylene group, both of which are defined herein.

The term "halo" refers to fluoro, chloro, bromo and iodo.

The term "heterocyclyl", "heterocyclic" or "heterocycle" means a non-aromatic saturated or partially saturated monocyclic, fused, bridged, or spiro bicyclic heterocyclic ring system(s). The term heterocyclyl includes both monovalent species and divalent species. Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or SO2 groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (═O) or thioxo (═S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example Advanced Organic Chemistry, by Jerry March, 4th Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

"Heterocyclyl(1-6C)alkyl" means a heterocyclyl group covalently attached to a (1-6C)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydro-pyrido[2,3-b]pyrazinyl and 3,4-dihydro-2H-pyrido[3,2-b][1,4]oxazinyl Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:

a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a 5- or 6-membered ring containing 1, 2 or 3 ring heteroatoms;
e) a pyrazole ring fused to a 5- or 6-membered ring containing 1 or 2 ring heteroatoms;
f) a pyrazine ring fused to a 5- or 6-membered ring containing 1 or 2 ring heteroatoms;
g) an imidazole ring fused to a 5- or 6-membered ring containing 1 or 2 ring heteroatoms;
h) an oxazole ring fused to a 5- or 6-membered ring containing 1 or 2 ring heteroatoms;
i) an isoxazole ring fused to a 5- or 6-membered ring containing 1 or 2 ring heteroatoms;
j) a thiazole ring fused to a 5- or 6-membered ring containing 1 or 2 ring heteroatoms;
k) an isothiazole ring fused to a 5- or 6-membered ring containing 1 or 2 ring heteroatoms;
l) a thiophene ring fused to a 5- or 6-membered ring containing 1, 2 or 3 ring heteroatoms;
m) a furan ring fused to a 5- or 6-membered ring containing 1, 2 or 3 ring heteroatoms;
n) a cyclohexyl ring fused to a 5- or 6-membered heteroaromatic ring containing 1, 2 or 3 ring heteroatoms; and
o) a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(1-6C)alkyl" means a heteroaryl group covalently attached to a (1-6C)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(1-6C)alkyl" means an aryl group covalently attached to a (1-6C)alkylene group, both of which are defined herein. Examples of aryl-(1-6C)alkyl groups include benzyl, phenylethyl, and the like This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

Wherever groups with large carbon chains are disclosed (e.g. (1-12C)alkyl, (1-8C)alkenyl, etc.), such groups may optionally be shortened, for instance containing a between 1 and 5 carbons (e.g. (1-5C)alkyl or (1-5C)alkenyl), or contain between 1 and 3 carbons (e.g. (1-3C)alkyl or (1-3C)alkenyl instead of (1-12C)alkyl or (1-8C)alkenyl).

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Compounds of formula I in which Z is $N^+$-Q in particular are cationic and will be associated with one or more counter anions. The compound of formula I possesses a +1 charge. The anion may carry a −1 charge, in which case the molar ratio of anion:cation is 1:1, or, alternatively, the anion may carry a −2 or −3 charge, in which case the molar ratio of anion:cation is will be 1:2 or 1:3, respectively.

In one embodiment, the anion is independently derived from one or more of the following acids: hydrochloric, hydrobromic, hydroiodic, sulfuric, sulfurous, nitric, nitrous, phosphoric, phosphorous acetic, propionic, succinic, gycolic, stearic, lactic, malic, tartaric, citric, ascorbic, maleic, hydroxymaleic, phenylacetic, glutamic, benzoic, salicylic, sulfanilic, 2-acetoxybenzoic, fumaric, toluenesulfonic, methanesulfonic, ethanesulfonic, ethane disulfonic, oxalic, isethionic, and valeric.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess telomerase inhibitory activity.

The present invention also encompasses compounds of the invention as defined herein which comprise one or more isotopic substitutions. For example, H may be in any isotopic form, including $^1$H, $^2$H(D) and $^3$H (T); C may be in any isotopic form, including $^{12}$C, $^{13}$C, and $^{14}$C; and O may be in any isotopic form, including $^{16}$O and $^{18}$O; and the like.

It is also to be understood that certain compounds of the formula I may exhibit polymorphism, and that the invention encompasses all such forms.

Compounds may exist in a number of different tautomeric forms and references to compounds include all such forms. For the avoidance of doubt, where a compound can exist in one of several tautomeric forms, and only one is specifically described or shown, all others are nevertheless embraced by the definition of the compound. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

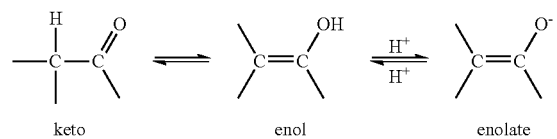

keto            enol            enolate

Compounds of the formula I containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with m-chloroperoxybenzoic acid (MCPBA), for example, in an inert solvent such as dichloromethane.

The compounds of formula I may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the formula I and in-vivo cleavable amide derivatives that may be formed at a carboxy group or an amino group in a compound of the formula I.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:—
a) Methods in Enzymology, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula I that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the formula I that possesses a hydroxy group is, for example, an in vivo cleavable ester or ether thereof. An in vivo cleavable ester or ether of a compound of the formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula I that possesses a carboxy group is, for example, an in vivo cleavable amide thereof, for example an amide formed with an amine such as ammonia, a $C_{1-4}$alkylamine such as methylamine, a $(C_{1-4}$alkyl$)_2$amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the formula I that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

It shall also be appreciated that compounds of formula I may also be covalently linked (at any suitable position) to other groups such as, for example, solubilising moieties (for example, PEG polymers), moieties that enable them to be bound to a solid support (such as, for example, biotin-containing moieties), and targeting ligands (such as antibodies or antibody fragments).

Topical Liquid Composition

The present invention provides a topical liquid composition, suitably as defined herein. Suitably the topical liquid composition is a liquid pharmaceutical composition for topical administration, suitably to a uterus, suitably to the uterus of a subject (suitably a female subject, suitably a mammalian subject, most suitably a human subject), suitably for use in assisted reproduction (which may include subjects with reduced fertility or subjects acting as surrogates).

The topical liquid composition suitably comprises a (pharmaceutically acceptable) diluent. Suitably the topical liquid composition is a liquid solution, most suitably an aqueous solution, suitably a solution that is (substantially) free of particulates.

The composition suitably comprises melatonin and/or an analog thereof (which whenever mentioned herein suitably includes any pharmaceutically acceptable salt and/or solvate of melatonin and/or an analog thereof).

The composition suitably comprises an active (suitably melatonin and/or an analog thereof) that either promotes embryonic implantation (e.g. during assisted reproduction treatments) or otherwise inhibits or prevents embryonic implantation failure (e.g. following transferral of one or more embryos to a uterus).

The composition suitably comprises a buffer system or a buffering agent. The composition suitably comprises a buffer system, and the pH of the composition is neutral or alkaline. Suitably the buffer system maintains the composition at a (substantially) constant pH (suitably varying by no more than +/−0.5 pH units, suitably by no more than +/−0.2 pH units, suitably by no more than +/−0.1 pH units) whilst inside the uterus. This may be established by measuring the pH of the composition before and after it has been utilised in uterine washing.

The composition suitably comprises one or more amino acids, suitably at least a first amino acid. The composition suitably comprises a second amino acid. Suitably the second amino acid is a different amino acid to any first amino acid. The composition suitably comprises at least one amino acid that comprises a sulphur atom, suitably a sulphur atom exhibiting a valency of 2 within said amino acid (e.g. a thiol or thioether). The composition suitably comprises at least one amino acid that is free of any sulphur atoms. Suitably the composition comprises (substantially) no more than two amino acids.

The composition suitably comprises a tonicifier. The tonicifier is suitably present to provide a composition having the desired osmolality or osmolarity, most suitably a osmolality that is within 20% of physiologically osmolality (i.e. blood plasma osmolality) of the relevant subject.

The composition suitably comprises a surfactant. The composition suitably comprises a surfactant that facilitates dissolution and/or dispersion of the active (e.g. melatonin) within the composition.

The composition may comprise a sugar or sugar alcohol.

The composition is suitably monophasic (i.e. a single liquid phase). Suitably the composition is free of any oil phase that is, at least to an extent, immiscible (e.g. forms a biphasic mixture) with water. Suitably the composition is not an oil-in-water or a water-in-oil composition.

The composition is suitably (substantially) free of any organic solvent(s), and is suitably free of any solvent(s) other than water. A solvent may be any suitable compound that exists in the liquid phase at SATP, and suitably remains liquid whilst temperature of the compound remains at or below 40° C., suitably 60° C., suitably 70° C. The composition is suitably (substantially) free of any (organic) solvents having a dielectric constant (or a "relative permittivity", which is readily measurable by those skilled in the art) may be readily measured less than or equal to 70, suitably less than or equal to 60, suitably less than or equal to 40, suitably less than or equal to 30. The composition is suitably (substantially) free of any (organic) solvents having a density less than or equal to 0.7 g/mL, suitably any solvents having a density less than oe equal to 0.8 g/mL, suitably any solvents having a density less than or equal to 0.9 g/mL. Suitably, the composition is (substantially) free of any (organic) solvents having a boiling point below 90° C. The composition is suitably (substantially) free of alcoholic solvents, such as ethanol.

Apart from the active(s) (e.g. melatonin), the composition is suitably (substantially) free of any components having a solubility in water (at SATP) less than or equal to 100 mg/L, suitably less than or equal to 1 g/L, suitably less than or equal to 10 g/L, suitably less than or equal to 20 g/L, most suitably less than or equal to 25 g/L.

The composition is suitably, especially prior to use and especially during storage, (substantially) free of any culture media/medium or else comprises no more than 1 wt % culture media/medium, suitably no more than 0.1 wt % culture media/medium, suitably no more than 0.001 wt % culture media/medium. Suitably, the composition may be used (e.g. for washing) without pre-mixing the composition within any culture media.

The composition is suitably, especially prior to use and especially during storage, (substantially) free of any protein or protein compounds, or else comprises no more than 1 wt % of any protein or protein compounds (collectively), suitably no more than 0.1 wt % of any protein or protein compounds, suitably no more than 0.001 wt % of any protein or protein compounds. The composition is suitably (substantially) free of any serum albumin (SA) or else comprises no more thereof than the amounts given above in relation to proteins and protein compounds. The composition is suitably (substantially) free of any human serum albumin (HSA).

The composition is suitably (substantially) free of polymers.

The composition is suitably (substantially) free of any selenium-containing compounds.

The composition may be suitably (substantially) free of any alkylene glycol (e.g. propylene glycol) compounds.

The active(s) (e.g. melatonin) suitably exhibits antioxidant properties.

Apart from the active(s) (e.g. melatonin), the composition is suitably (substantially) free of any amino acids bearing a substituted terminal amino group (e.g. bearing an N-acylated or N-acetylated terminal amino group). Suitably, the composition is (substantially) free of N-acetylcysteine (or any salts and/or derivatives thereof, e.g. esters).

The composition may suitably include any one or more additional components defined herein in relation to a topical liquid composition (e.g. including surfactant, tonicifier, etc.), optionally in any amount, concentration, or form stipulated herein; and wherein the composition optionally exhibits any one or more parameters or properties given herein in relation to a topical liquid composition (e.g. pH, osmolality).

Advantageously, the present invention provides topical liquid compositions that not only serve as excellent and clinically safe washing/irrigation compositions for use within a uterus (suitably to prepare the uterus for receiving an embryo and to facilitate the implantation of the embryo within the uterus—the compositions of the invention certain exhibit excellent implantation success rates) but also exhibit excellent stability properties (for all stages of its production, storage, shipping and use). The provision of such stable formulations represents a significant advance because these high-performing formulations are now rendered practical, not least in view of the storage and transport considerations. Such formulations are provided at minimal cost and with minimal technical complexity.

In a particular embodiment, the topical liquid composition comprises:
- melatonin (N-acetyl-5-methoxytryptamine) and/or an analog thereof, or a pharmaceutically acceptable salt or solvate thereof; and
- a phosphate buffer system.

In a particular embodiment, the topical liquid composition comprises:
- melatonin (N-acetyl-5-methoxytryptamine) and/or an analog thereof, or a pharmaceutically acceptable salt or solvate thereof; and
- a phosphate buffer system; and
- at least one amino acid (suitably a natural amino acid, suitably selected from methionine, cysteine, arginine, and glycine, or a combination of any or all of the aforementioned).

In a particular embodiment, the topical liquid composition comprises:
- melatonin (N-acetyl-5-methoxytryptamine) and/or an analog thereof, or a pharmaceutically acceptable salt or solvate thereof; and
- a phosphate buffer system; and
- at least two amino acids (suitably natural amino acids, suitably selected from methionine, cysteine, arginine, and glycine, or a combination of any or all of the aforementioned).

In a particular embodiment, the topical liquid composition comprises:
- melatonin (N-acetyl-5-methoxytryptamine) and/or an analog thereof, or a pharmaceutically acceptable salt or solvate thereof; and
- a phosphate buffer system; and
- a first amino acid (suitably a natural amino acid, suitably selected from methionine or cysteine), suitably as defined herein; and
- a second amino acid (suitably a natural amino acid, suitably selected from arginine or glycine, though most suitably arginine), suitably as defined herein.

In a particular embodiment, the topical liquid composition comprises:
- melatonin (N-acetyl-5-methoxytryptamine) and/or an analog thereof, or a pharmaceutically acceptable salt or solvate thereof; and
- a phosphate buffer system; and
- a first amino acid, which is suitably an amino acid comprising at least one sulphur atom (suitably a divalent sulphur atom, such as a thiol or thioester), most suitably either methionine or cysteine (though any of these may be provided in a salt form).

In a particular embodiment, the topical liquid composition comprises:
- melatonin (N-acetyl-5-methoxytryptamine) and/or an analog thereof, or a pharmaceutically acceptable salt or solvate thereof; and
- a phosphate buffer system; and
- a tonicifier, suitably of a type and in an amount sufficient for the osmolality of the composition to be between 250-350 mOsm/kg.

In a particular embodiment, the topical liquid composition comprises:
- melatonin (N-acetyl-5-methoxytryptamine) and/or an analog thereof, or a pharmaceutically acceptable salt or solvate thereof; and
- a phosphate buffer system; and
- a first amino acid, which is suitably an amino acid comprising at least one sulphur atom (suitably a divalent sulphur atom, such as a thiol or thioester), most suitably either methionine or cysteine (though any of these may be provided in a salt form); and
- a tonicifier, suitably of a type and in an amount sufficient for the osmolality of the composition to be between 250-350 mOsm/kg.

In a particular embodiment, the topical liquid composition comprises:
- melatonin (N-acetyl-5-methoxytryptamine) and/or an analog thereof, or a pharmaceutically acceptable salt or solvate thereof; and
- a phosphate buffer system;
- a surfactant, most suitably a non-ionic surfactant; and
- either or both a first amino acid and/or a second amino acid, wherein suitably a first amino acid is an amino acid comprising at least one sulphur atom; and a second amino acid is suitably free of any sulphur atoms.

In a particular embodiment, the topical liquid composition comprises:
- melatonin (N-acetyl-5-methoxytryptamine) and/or an analog thereof, or a pharmaceutically acceptable salt or solvate thereof; and
- a phosphate buffer system;
- a tonicifier, suitably of a type and in an amount sufficient for the osmolality of the composition to be between 250-350 mOsm/kg; and
- optionally a surfactant, most suitably a non-ionic surfactant, where said surfactant is present in combination with either or both a first amino acid and/or a second amino acid, wherein suitably a first amino acid is an amino acid comprising at least one sulphur atom; and a second amino acid is suitably free of any sulphur atoms.

In a particular embodiment, the topical liquid composition comprises:
- 1-200 ng/mL melatonin (N-acetyl-5-methoxytryptamine) and/or an analog thereof, or a pharmaceutically acceptable salt or solvate thereof; and
- a buffer system (suitably a phosphate buffer system, suitably a buffer system at a concentration of 1-100 mM, suitably a phosphate buffer system at a concentration 0.098-9.8 mg/mL in terms of phosphoric acid equivalents);

wherein the composition has a pH between 7.0 and 8.5.

In a particular embodiment, the topical liquid composition comprises:
- 1-200 ng/mL melatonin (N-acetyl-5-methoxytryptamine) and/or an analog thereof, or a pharmaceutically acceptable salt or solvate thereof; and
- a buffer system (suitably a phosphate buffer system, suitably a buffer system at a concentration of 1-100 mM, suitably a phosphate buffer system at a concentration 0.098-9.8 mg/mL in terms of phosphoric acid equivalents);

wherein the composition has an osmolality between 250-350 mOsm/kg.

Melatonin and/or Analogs

The topical liquid composition suitably comprises an active ingredient, suitably one that is capable of exhibiting the properties required to carry out one of the methods of treatment defined herein. Suitably, the active ingredient is melatonin (N-acetyl-5-methoxytryptamine) and/or an analog thereof, or a pharmaceutically acceptable salt or solvate thereof.

Any suitable analog of melatonin that delivers the desired properties may be employed within the topical liquid composition. The melatonin and/or analog thereof is suitably a compound having an affinity a melatonin receptor (a G protein-coupled receptor (GPCR) that binds melatonin). Suitably, the melatonin and/or analog thereof is a melatonin receptor agonist. Suitably, the melatonin and/or analog thereof is a $MT_1$ (or $Mel_{1A}$ or MTNR1A) and/or $MT_2$ (or $Mel_{1B}$ or MTNR1B) receptor agonist.

A number of melatonin analogs are known in the art. Melatonin itself has the following Formula:

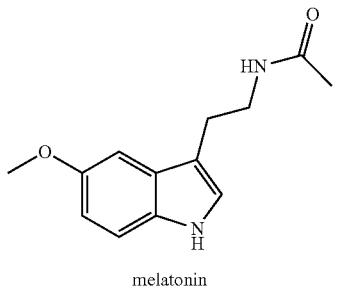 [SMILES: COc1ccc2[nH]cc(CCNC(C)=O)c2c1]

melatonin

In an embodiment, the active ingredient (melatonin and/or analogs thereof) is defined by Formula I:

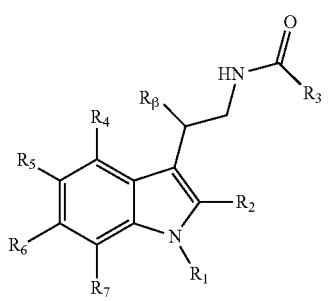

Formula I wherein:
$R_1$ is selected from hydrogen or an $R_{HET}$ group;
$R_2$ is selected from hydrogen, halogeno, trifluoromethyl, cyano, isocyano, nitro, hydroxy, mercapto, amino, formyl, carboxy, carbamoyl, ureido, or an $R_C$ group;
$R_3$ is selected from hydrogen or an $R_C$ group;
$R_4$ is selected from hydrogen, an $R_C$ group, or $R_4$ is linked to $R_5$ such that, together with the carbon atoms to which $R_4$ and $R_5$ are attached, they form a carbocyclic, heterocyclic, aryl, or heteroaryl ring system;
$R_5$ is selected from an $R_C$ group, or $R_5$ is linked to $R_4$ such that, together with the carbon atoms to which $R_4$ and $R_5$ are attached, they form a carbocyclic, heterocyclic, aryl, or heteroaryl ring system;
$R_6$ is selected from hydrogen, halogeno, trifluoromethyl, cyano, isocyano, nitro, hydroxy, mercapto, amino, formyl, carboxy, carbamoyl, ureido, or an $R_C$ group;
$R_7$ is selected from hydrogen or an $R_C$ group;
$R_\beta$ is selected from hydrogen, halogeno, trifluoromethyl, cyano, isocyano, nitro, hydroxy, mercapto, amino, formyl, carboxy, carbamoyl, ureido, or an $R_C$ group;
wherein any $R_1$, $R_2$, $R_3$, $R_4$, $R_5$, $R_6$, $R_7$, $R_\beta$ group, or any ring system formed via any of the aforesaid groups being linked together, is (to the extent it is structurally possible—e.g. any CH, $CH_2$, or $CH_3$ group thereof) optionally independently substituted with one or more $R_{sub}$ groups;
or a pharmaceutically acceptable salt and/or solvate thereof.

$R_1$ is suitably hydrogen or (1-3C)alkyl, optionally substituted as defined herein. Suitably $R_1$ is hydrogen.
$R_2$ is suitably selected from hydrogen, halogeno, or an $R_C$ group, optionally substituted as defined herein. $R_2$ is suitably selected from hydrogen, bromo, iodo, or aryl, optionally substituted as defined herein. $R_2$ is suitably selected from hydrogen, bromo, iodo, or phenyl, optionally substituted as defined herein. $R_2$ is suitably hydrogen.
$R_3$ is suitably an $R_C$ group, optionally substituted as defined herein. $R_3$ is suitably (1-6C)alkyl, optionally substituted as defined herein, most suitably $R_3$ is methyl.
$R_4$ is suitably selected from hydrogen or $R_4$ is linked to $R_5$ such that, together with the carbon atoms to which $R_4$ and $R_5$ are attached, they form a heterocyclic or heteroaryl ring system, optionally substituted as defined herein. $R_4$ is suitably selected from hydrogen or $R_4$ is linked to $R_5$ such that, together with the carbon atoms to which $R_4$ and $R_5$ are attached, they form a heterocyclic ring system, optionally substituted as defined herein. $R_4$ is suitably selected from hydrogen or $R_4$ is linked to $R_5$ such that, together with the carbon atoms to which $R_4$ and $R_5$ are attached, they form a 5-membered heterocyclic ring system comprising a single internal oxygen atom (which is suitably attached directly to the carbon to which $R_5$ is directly attached), optionally substituted as defined herein.
$R_5$ is suitably selected from an $R_C$ group, or $R_5$ is linked to $R_4$ such that, together with the carbon atoms to which $R_4$ and $R_5$ are attached, they form a heterocyclic or heteroaryl ring system, optionally substituted as defined herein. $R_5$ is suitably selected from an $R_C$ group, or $R_5$ is linked to $R_4$ such that, together with the carbon atoms to which $R_4$ and $R_5$ are attached, they form a heterocyclic ring system, optionally substituted as defined herein. $R_5$ is suitably selected from an $R_C$ group, optionally substituted as defined herein. $R_5$ is suitably selected from an $R_C$ group comprising an oxygen atom which is attached directly to the carbon to which $R_5$ is directly attached. Most suitably $R_C$ is (1-3C)alkoxy, most suitably methoxy.
$R_6$ is suitably selected from hydrogen, halogeno, or an $R_C$ group, optionally substituted as defined herein. $R_6$ is suitably selected from hydrogen, halogeno, or an $R_C$ group comprising an oxygen atom which is attached directly to the carbon to which $R_6$ is directly attached. $R_6$ is suitably selected from hydrogen, halogeno, or (1-6C)alkanoyloxy, optionally substituted as defined herein. $R_6$ is suitably hydrogen.
$R_7$ is suitably hydrogen.
$R_\beta$ is suitably selected from hydrogen, halogeno, or an $R_C$ group, optionally substituted as defined herein. $R_\beta$ is suitably selected from hydrogen, halogeno, or (1-3C)alkyl, optionally substituted as defined herein. $R_\beta$ is suitably hydrogen.

In an embodiment, melatonin and its analog(s) is defined by Formula II:

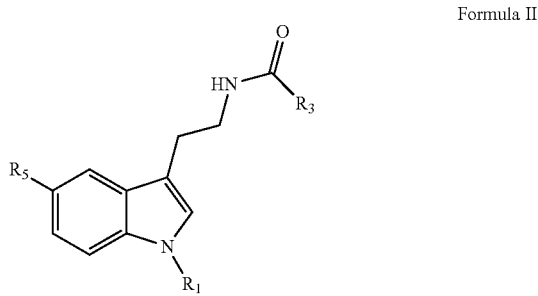

Formula II wherein $R_1$, $R_3$, and $R_5$ have any of the aforementioned definitions;

or a pharmaceutically acceptable salt and/or solvate thereof.

Each $R_{HET}$ group is independently selected from trifluoromethyl, carboxy, carbamoyl, ureido, (1-12C)hydrocarboyl, (1-12C)alkanoyl, (3-10C)carbocyclyl, heterocyclyl, aryl, heteroaryl, (3-10C)carbocyclyl-(1-12C)hydrocarboyl, heterocyclyl-(1-12C)hydrocarboyl, aryl-(1-12C)hydrocarboyl, heteroaryl-(1-12C)hydrocarboyl, or a group defined by the Formula:

$$L_1\text{-}X_1$$

wherein $L_1$ is a direct bond or is selected from $[C(R_{1a})(R_{1b})]_n$, SO, $SO_2$, CO, $CH(OR_{1a})$, $CON(R_{1a})$, $SO_2N(R_{1a})$, wherein n is an integer between 1 and 4, and $R_{1a}$ and $R_{1b}$ are each independently selected from hydrogen or (1-8C)alkyl; and $X_1$ is selected from hydrogen, trifluoromethyl, carboxy, carbamoyl, ureido, (1-12C)hydrocarboyl, (1-12C)alkanoyl, (3-10C)carbocyclyl, heterocyclyl, aryl, heteroaryl, (3-10C)carbocyclyl-(1-12C)hydrocarboyl, heterocyclyl-(1-12C)hydrocarboyl, aryl-(1-12C)hydrocarboyl, and heteroaryl-(1-12C)hydrocarboyl;

wherein each $R_{HET}$ is independently optionally substituted by one or more groups independently selected from $R_{sub}$.

Each $R_C$ group is independently selected from trifluoromethyl, (1-12C)hydrocarboyl, (3-10C)carbocyclyl, heterocyclyl, aryl, heteroaryl, (3-10C)carbocyclyl-(1-12C)hydrocarboyl, heterocyclyl-(1-12C)hydrocarboyl, aryl-(1-12C)hydrocarboyl, heteroaryl-(1-12C)hydrocarboyl, or a group defined by the Formula:

$$L_2\text{-}X_2$$

wherein $L_2$ is a direct bond or is selected from $[C(R_{2a})(R_{2b})]_n$, O, S, $N(R_{2a})$, $CH(OR_{2a})$, $N(R_{2a})CO$, $N(R_{2a})CON(R_{2b})$, $N(R_{2a})SO_2$, $OC(R_{2a})_2$, $SC(R_{2a})_2$ and $N(R_{2a})C(R_{2b})_2$, wherein n is an integer between 1 and 4 and wherein $R_{2a}$ and $R_{2b}$ are independently selected from hydrogen or (1-8C)alkyl; and $X_2$ is selected from hydrogen, trifluoromethyl, carboxy, carbamoyl, ureido, (1-12C)hydrocarboyl, (1-12C)alkanoyl, (3-10C)carbocyclyl, heterocyclyl, aryl, heteroaryl, (3-10C)carbocyclyl-(1-12C)hydrocarboyl, heterocyclyl-(1-12C)hydrocarboyl, aryl-(1-12C)hydrocarboyl, and heteroaryl-(1-12C)hydrocarboyl;

wherein each $R_C$ is independently optionally substituted by one or more groups independently selected from $R_{sub}$.

Each $R_{sub}$ group is independently selected from halogeno, trifluoromethyl, cyano, isocyano, nitro, hydroxy, mercapto, amino, formyl, carboxy, carbamoyl, ureido, (1-12C)hydrocarboyl, (3-10C)carbocyclyl, heterocyclyl, aryl, heteroaryl, (3-10C)carbocyclyl-(1-12C)hydrocarboyl, heterocyclyl-(1-12C)hydrocarboyl, aryl-(1-12C)hydrocarboyl, heteroaryl-(1-12C)hydrocarboyl, or a group defined by the Formula:

$$L_3\text{-}X_3$$

wherein $L_3$ is a direct bond or is selected from $[C(R_{3a})(R_{3b})]_n$, O, S, $N(R_{3a})$, $CH(OR_{3a})$, $N(R_{3a})CO$, $N(R_{3a})CON(R_{3b})$, $N(R_{3a})SO_2$, $OC(R_{3a})_2$, $SC(R_{3a})_2$ and $N(R_{3a})C(R_{3b})_2$, wherein n is an integer between 1 and 4 and wherein $R_{3a}$ and $R_{3b}$ are independently selected from hydrogen or (1-8C)alkyl; and $X_3$ is selected from hydrogen, trifluoromethyl, carboxy, carbamoyl, ureido, (1-12C)hydrocarboyl, (1-12C)alkanoyl, (3-10C)carbocyclyl, heterocyclyl, aryl, heteroaryl, (3-10C)carbocyclyl-(1-12C)hydrocarboyl, heterocyclyl-(1-12C)hydrocarboyl, aryl-(1-12C)hydrocarboyl, and heteroaryl-(1-12C)hydrocarboyl;

wherein each $R_{sub}$ is itself independently optionally substituted by one or more groups independently selected from $R_{sub}$.

Suitably:

$R_1$ is hydrogen or (1-3C)alkyl, most suitably hydrogen;

$R_2$ is hydrogen or (1-3C)alkoxy, most suitably (1-3C)alkoxy, most suitably methoxy; and $R_3$ is hydrogen or (1-6C)alkyl, most suitably (1-3C)alkyl, most suitably methyl.

In a particular embodiment, the compound off Formula I is melatonin or a pharmaceutically acceptable salt and/or solvate thereof.

In an embodiment, the melatonin or melatonin analog(s) may be selected from melatonin, ramelteon, agomelatine, tasimelteon, and LY-156735 (TIK-301), or a pharmaceutically acceptable salt and/or solvate thereof.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

It is also to be understood that certain compounds of the formula I may exist in solvated as well as unsolvated forms such as, for example, hydrated forms.

In an embodiment, the topical liquid composition comprises the active ingredient (melatonin and/or a melatonin analog) at a concentration of from about 2 to about 200 ng/ml (nanograms per milliliter), suitably from about 5 to about 30 ng/mL, more suitably from about 15 to 25 ng/mL, most suitably about 20 ng/mL. However, in certain embodiments, the topical liquid composition is a concentrated the topical liquid composition wherein the active ingredient may be present at a concentration that is five times higher than the aforementioned concentration ranges, though suitably any other components present within the (concentrated) topical liquid composition are also present at five times the concentration stipulated in relation to standard topical liquid compositions. As such, the topical liquid composition may comprise the active ingredient (melatonin and/or a melatonin analog) at a concentration of from about 10 to about 1000 ng/ml, with any of the aforementioned ranges calculated accordingly with a five times multiplier.

Buffer Systems and pH

Suitably, the topical liquid composition is a buffered solution whose pH is stabilised by a buffering agent (or a buffer system), suitably in combination with an acid/base conjugate of the buffering agent. As such, the topical liquid composition suitably comprises a buffering agent (or at least one buffering agent) as defined herein. Preferably, the topical liquid composition additionally comprises an acid/base conjugate, wherein said acid/base conjugate corresponds to the conjugate acid or conjugate base of the buffering agent, depending on whether the buffering agent is itself a base or acid respectively. Collectively, the buffering agent and its acid/base conjugate (which may be plural in some cases, such as phosphate buffer systems which comprise numerous buffering species) may be considered a "buffer system". The topical liquid composition thus suitably comprises a "buffer system" (suitably comprising a buffering agent(s) and an acid/base conjugate(s) thereof), and any concentrations stipulated in relation to the buffer system generally relate to the combined concentrations of the buffering agent(s) and any acid/base conjugate(s) thereof. Any "buffer system" suitably comprises a weak acid and a weak base (see above definitions).

Suitably, the buffering agent is a phosphate buffering agent. Suitably the phosphate buffering agent is a phosphate (or hydrogenphosphate salt), suitably comprising anionic phosphate species and one or more pharmaceutically acceptable countercations. A suitable phosphate salt may include a metal phosphate salt (e.g. an alkali metal phosphate or an alkaline earth metal phosphate, which may include one or more of the various hydrogen phosphates), or a non-metal phosphate salt (e.g. ammonium phosphate, triethylammonium phosphate, which may include one or more of the various hydrogen phosphates). In a particular embodiment, the buffering agent (and the phosphate salt) comprises sodium phosphate(s) (which may include sodium hydrogen phosphate and/or sodium dihydrogen phosphate as well as optionally including trisodium phosphate).

Suitably, the topical liquid composition comprises an acid/base conjugate(s) of the buffering agent(s), most suitably phosphoric acid (or a hydrogen phosphate) as the conjugate acid of a phosphate salt. The combination of the buffering agent(s) and its acid/base conjugate(s) constitute a buffer system. Suitably, the topical liquid composition comprises the buffering agent(s) and its corresponding acid/base conjugate(s), suitably such that together the buffering agent(s) and its acid/base conjugate(s) are present at a level (i.e. absolute amount or concentration) and in a relative amount (or concentration) sufficient to provide the desired pH for the composition. The buffer system may be formed in a variety of ways, especially where phosphate buffer systems are concerned, where multiple buffering species may be present. The buffer system may be formed by simply mixing the buffering agent(s) with its acid/base conjugate(s) or may alternatively be formed by mixing an acid or base with either the buffering agent(s) or its acid/base conjugate(s) in order to form in situ the desired mixture of buffering agent(s) and acid/base conjugate(s). For example, the buffer system may be formed by simply mixing a phosphate buffering agent (e.g. sodium phosphate and/or related hydrogen phosphate(s)) with its acid/base conjugate (i.e. phosphoric acid) or indeed with a strong acid (e.g. hydrochloric acid), suitably in a ratio appropriate to furnish the desired pH. Alternatively, the buffer system may be formed by adding a base (e.g. sodium hydroxide) to the acid/base conjugate (i.e. phosphoric acid and/or related hydrogen phosphate(s)) of the phosphate buffering agent, suitably in an amount appropriate to furnish the desired pH and mixture of the buffering agent (e.g. sodium phosphate(s)) and corresponding acid/base conjugate(s) (i.e. phosphoric acid). Alternatively, either method of forming the buffer system may be employed, and pH may be judiciously adjusted by either adding further acid (suitably strong acid, such as HCl) or further base (suitably strong base, such as sodium hydroxide).

Most suitably, the buffer system is or at least comprises a phosphate buffer system, suitably comprising a mixture of one or more phosphate salts (suitably selected from tribasic phosphate salts, dibasic hydrogen phosphate salts, or monobasic dihydrogen phosphate salts) and/or phosphoric acid.

In some embodiments, the buffer system comprises two or more buffer systems, for example a phosphate buffer system and a histidine buffer system. In respect of the phosphate buffer system, the buffering agent and buffering species may be as described above. Suitably, the buffering agent of the histidine buffer is an histidine buffering agent. Suitably the histidine buffering agent is histidine (or a salt thereof), most suitably free histidine (e.g. zwitterionic histidine). A histidine buffer is less straightforward than many other common phosphate or carboxylate buffer systems, since the imidazole moiety of histidine means that histidine generally exists in aqueous solution as an equilibrium mixture of protonated (imidazolium) and deprotonated (free imidazole) forms at pHs between pH6-7. The protonated (imadazolium) form of histidine may be associated with one or more pharmaceutically acceptable anions—including anions such as hydroxide or chloride—though the imidazolium form may additionally or alternatively exist in a diluent (e.g. water) as a solvated cation. As such, the protonated (imidazolium) form of histidine may be considered to be histidine's acid/base conjugate, since it represents the conjugate acid of histidine. This conjugate acid of histidine suitably has both the amino and imidazole group protonated but carboxylate group deprotonated—this gives a net positively charge of +1). The combination of the buffering agent and its acid/base conjugate constitutes a buffer system. A histidine buffer system may be formed following the same or similar principles as per the phosphate buffer system, and where phosphate and histidine buffer systems co-exist within a topical liquid composition, suitably the buffer systems are established with a desired pH, and where necessary strong acid or strong base is added to make fine pH adjustments.

However, in many embodiments there is only a single buffer system, most suitably a phosphate buffer system.

Suitably, the topical liquid composition comprises at most one buffer system, which is most suitably a phosphate buffer system.

Suitably, the topical liquid composition has a pH greater than or equal to pH 6.5, suitably greater than or equal to pH 7.0, more suitably greater than or equal to pH 7.5, most suitably greater than or equal to pH 7.6.

Suitably, the topical liquid composition has a pH less than or equal to pH 9.0, suitably less than or equal to pH 8.5, more suitably less than or equal to pH 7.9, more suitably less than or equal to pH 7.8.

Most suitably, the topical liquid composition has a pH between pH 7.0 and 8.5, more suitably between 7.5 and 7.9, most suitably between 7.6 and 7.8. Within these pH ranges, the predominant buffering species present within a phosphate buffer system are monohydrogen phosphate and dihydrogen phosphate.

Suitably, the topical liquid composition comprises a buffer system (suitably a phosphate buffer system, suitably comprising a phosphate buffering agent) at a concentration of from about 0.01 to 100 mM, suitably from about 1 to 50 mM, more suitably from about 5 to 15 mM, most suitably about 10 mM. Suitably, the topical liquid composition comprises a phosphate buffer system comprising two or more buffering species selected from phosphoric acid, dihydrogenphosphate, monohydrogenphosphate, and phosphate (and/or derivatives thereof—e.g. o-phosphoric acid), suitably with sodium counterions to any phosphate species, at a collective concentration of from about 0.01 to 100 mM, suitably from about 1 to 50 mM, more suitably from about 5 to 15 mM, most suitably about 10 mM. In preferred embodiments, the predominant phosphate buffering species are monohydrogen phosphate and dihydrogen phosphate.

Suitably, where more than one buffer system is present (e.g. a histidine buffer system as well as a phosphate buffer system) each of the first and second buffer systems are present at the aforementioned concentrations (e.g. so that the total concentration of the buffer system may be doubled).

Suitably, the topical liquid composition comprises a phosphate buffer system wherein the phosphate buffering species are present within the composition at a concentration (defined by reference to phosphoric acid equivalents, i.e. hypothetically assuming all of the buffering species are in the phosphoric acid form, MW=98) of from about 0.98 μg/mL to 9.8 mg/mL (i.e. 0.98 μg/mL to 9.8 mg/mL of phosphoric acid equivalents), suitably from about 0.098 mg/mL to about 4.9 mg/mL, suitably from about 0.49 mg/mL to about 1.47 mg/mL, most suitably about 0.98 mg/mL.

Suitably, the weight ratio of phosphate buffering species (in terms of phosphoric acid equivalents) to melatonin and/or a melatonin analog within the topical liquid composition is between 1,000,000:1 and 500:1, suitably between 500,000:1 and 5,000:1, suitably between 25,000:1 and 75,000:1, suitably about 50,000:1.

Amino Acids

The topical liquid composition suitably comprises one or more amino acids, suitably two amino acids. Each, some, or all such amino acids are suitably natural amino acids. Such amino acid(s) may be suitably provided in zwitterionic form or a salt form (e.g. arginine.HCl salt, and/or cysteine.HCl salt). Suitably, unless stated otherwise, any amounts or concentrations (whether absolute or relative) given herein in relation to amino acids suitably refer to the amounts or concentrations of the respective free zwitterionic amino acids, even though said amino acids may be provided in a different form or may even exist within the topical liquid composition in a different form at the prevailing pH.

The topical liquid composition suitably comprises a first amino acid, which is suitably a natural amino acid. The first amino acid suitably comprises at least one sulphur atom, and suitably at most one sulphur atom. Suitably the sulphur atom in question is a divalent sulphur atom (suitably excluding sulphonic acids and such like, and suitably excluding amino acids such as taurine). Suitably the divalent sulphur atom is associated with a thiol or thioester moiety. As such, the first amino acid suitably comprises a thiol (—SH, mercapto group) or thioester (—SR, organosulfanyl group). Suitably the thioester is a group selected from (1-12C)alkylsulfanyl, (3-8C)cycloalkylsulfanyl, arylsulfanyl, aryl-(1-3C)alkylsulfanyl, heteroarylsulfanyl, heteroaryl-(1-3C)alkylsulfanyl, optionally substituted by one or more $R_{sub}$ groups as defined herein. More suitably, the thioester is a group selected from (1-3C)alkylsulfanyl or arylsulfanyl, more suitably (1-3C) alkylsulfanyl, most suitably methylsulfanyl. In a particular embodiment, the first amino acid is selected from methionine and cysteine. In a preferred embodiment, the first amino acid is methionine.

Suitably, the topical liquid composition comprises a first amino acid (suitably selected from methionine or cysteine, most suitably methionine) at a concentration of from about $1\times10^{-6}$ to 5 mg/mL, suitably from about 0.001-1.0 mg/mL, from about 0.005-0.015 mg/mL, most suitably about 0.01 mg/mL.

Suitably, the topical liquid composition comprises a first amino acid (suitably selected from methionine or cysteine) at a concentration of from about 6.7 nM to 33.5 mM, suitably from about 0.0067 to 6.7 mM, more suitably from about 0.0335 to 0.1 mM, most suitably about 0.067 mM.

The topical liquid composition suitably comprises a second amino acid, which is suitably a natural amino acid, suitably though not necessarily in addition to a first amino acid (suitably a first amino acid as defined herein). Suitably, where a first amino acid is also present, the first and second amino acids are different. The second amino acid is suitably free of any sulphur atoms, suitably free of any thiol or thioester groups, especially those defined herein in relation to a first amino acid. The second amino acid is suitably a basic amino acid, suitably a basic natural amino acid (i.e. selected from one of arginine, lysine, or histidine). However, where the topical liquid composition comprises histidine, such histidine suitably performs the role or is comprised of the buffer system. In a preferred embodiment, the second amino acid is selected from glycine or arginine, most suitably arginine. Suitably the second amino acid is provided as an acid salt thereof (i.e. rather than the standard neutral zwitterionic species), such as the hydrochloride salt thereof. However, suitably any amounts or concentrations relate to the free zwitterionic form of the second amino acid, regardless of the salt form in which it is provided or exists within the topical liquid composition.

Suitably, the topical liquid composition comprises a second amino acid (suitably selected from arginine or glycine, most suitably arginine) at a concentration of from about 0.0008-8 mg/mL (suitably provided as about 0.001-10 mg/mL arginine.HCl), suitably from about 0.008-0.8 mg/mL (suitably provided as about 0.01-1.0 mg/mL arginine.HCl), from about 0.04-0.4 mg/mL (suitably provided as about 0.05-0.5 mg/mL arginine.HCl), most suitably about 0.082-0.084 mg/mL (suitably provided as 0.1 mg/mL arginine.HCl).

Suitably, the topical liquid composition comprises a second amino acid (suitably arginine) at a concentration of from about 0.00475 to 47.5 mM, suitably from about 0.0475 to 4.75 mM, more suitably from about 0.238 to 2.38 mM, most suitably about 0.475 mM.

Suitably, the composition may be (substantially) free of further amino acids other than those stipulated or else comprise no more than 0.1 mM of any individual further amino acid, suitably no more than 0.01 mM of any individual further amino acid, suitably no more than 0.001 mM of any further individual amino acid.

In a particular embodiment, the composition comprises both one sulphur-containing amino acid and one non-sulphur-containing amino acid and is (substantially) free of any further amino acids or comprises any further amino acids at an individual concentration (with respect to each amino acid) of no more than 0.1 mM, suitably no more than 0.01 mM, suitably no more than 0.001 mM. In such embodiments, most suitably the sulphur-containing amino acid is methionine and the non-sulphur-containing amino acid is arginine.

Tonicifiers and Osmolality

The composition suitably comprises a tonicifier. The tonicifier is suitably present to provide the topical liquid composition with the desired osmolality or osmolarity, most suitably a osmolality that is within 20% of physiologically osmolality (i.e. blood plasma osmolality) of the relevant subject. Suitably a tonicifier is present within the composition in a quantity or concentration sufficient for the composition to be (substantially) isotonic with body fluids. Suitably a tonicifier is present within the composition in a quantity or concentration sufficient for the composition to have an osmolarity or osmolality within a range defined herein.

Any suitable tonicifier may be used. However, suitably the tonicifier is selected from the group including water-soluble metal salts (e.g. sodium chloride, potassium chloride, magnesium chloride, calcium chloride), water-soluble tonicifying sugars/sugar alcohols (e.g. glucose, sucrose, mannitol), and/or other water-soluble polyols. Suitably the tonicifier(s) is non-buffering (i.e. gives rise to little or no buffering effect). As such, any metal salt tonicifiers are suitably not buffering agents.

The topical liquid composition may comprise one or more tonicifiers, though preferably only a single "tonicifier" as such is present (notwithstanding any tonicifying effects imparted to the composition by components intended to serve another function as defined herein).

Most preferably, the tonicifier is or comprises a metal salt (preferably a non-buffering water-soluble metal salt). Suitably, said metal salt is or comprises a metal halide, suitably an alkali or an alkaline earth metal halide, suitably an alkali metal chloride.

In a particular embodiment, the tonicifier is or comprises sodium chloride. In a particular embodiment, the tonicifier is sodium chloride. Sodium chloride is a particularly advantageous stabiliser for use alongside a phosphate and/or histidine buffer system in liquid melatonin formulations.

Suitably, the topical liquid composition comprises the tonicifier(s) (most suitably sodium chloride) at a concentration of from about 1 mg/mL to about 100 mg/mL, more suitably from about 2 mg/mL to about 30 mg/mL, more suitably from about 5 mg/mL to about 12 mg/mL. In an embodiment, the tonicifier(s) is present at a concentration of about 9 mg/mL.

Suitably, the topical liquid composition comprises the tonicifier(s) (most suitably sodium chloride) at a concentration of from about 17 to about 1,711 mM, more suitably from about 34 to about 513 mM, more suitably from about 85.5 to about 205 mM. In an embodiment, sodium chloride is present at a concentration of 154 mM.

The topical liquid composition of the present invention suitably has an osmolality of 150-400 mOsm/kg, suitably 250-350 mOsm/kg, suitably 280-330 mOsm/kg, suitably 295-320 mOsm/kg, suitably 300-315 mOsm/kg.

Surfactants

The topical liquid composition of the invention may comprise a surfactant or one or more surfactants, suitably as defined herein.

Any suitable surfactant may be used. However, suitably the surfactant is a non-ionic surfactant, most suitably a polysorbate (polyoxyethylene glycol sorbitan alkyl esters) or span (sorbitan alkyl esters) surfactant, though alternatively the non-ionic surfactant may be an alkylene glycol (e.g. propylene glycol) or a polyalkylene glycol (e.g. diethylene glycol).

Though one or more surfactants may be included within the topical liquid composition of the invention, most suitably only a single surfactant is present, most suitably a single non-ionic surfactant (suitably as defined herein).

The surfactant(s) are suitably selected from Polysorbate 20 (Polyoxyethylene (20) sorbitan monolaurate), Polysorbate 40 (Polyoxyethylene (20) sorbitan monopalmitate), Polysorbate 60 (Polyoxyethylene (20) sorbitan monostearate), Polysorbate 80 (Polyoxyethylene (20) sorbitan monooleate), Sorbitan monolaurate, Sorbitan monopalmitate, Sorbitan monostearate, Sorbitan tristearate, and/or Sorbitan monooleate.

In a particular embodiment, the surfactant(s) are selected from Polysorbate 20, Polysorbate 40, Polysorbate 60, and/or Polysorbate 80. In a particular embodiment, the topical liquid composition comprises a single surfactant selected from Polysorbate 20, Polysorbate 40, Polysorbate 60, and Polysorbate 80.

In a particular embodiment, the surfactant is polysorbate 20.

Suitably, the topical liquid composition comprises the surfactant(s) (most suitably polysorbate 20) at a concentration of from about 0.001 mg/mL to about 10 mg/mL, more suitably from about 0.01 mg/mL to about 1 mg/mL, more suitably from about 0.025 mg/mL to about 0.075 mg/mL. In an embodiment, the surfactant(s) is present at a concentration of about 0.05 mg/mL. In a particular embodiment, polysorbate 20 is present at a concentration of about 0.05 mg/mL.

Suitably, the topical liquid composition comprises the surfactant(s) (most suitably polysorbate 20) at a concentration of from about 0.0008 to about 8 mM (i.e. 0.1 µM-5 mM), more suitably from about 0.008 to about 0.8 mM, more suitably from about 0.02 to about 0.06 mM. In an embodiment, the surfactant(s) is present at a concentration of about 0.04 mM. In an embodiment, polysorbate 20 is present at a concentration of 0.04 mM.

Where the surfactant(s) is or comprises an alkylene glycol or polyalkylene glycol (especially propylene glycol), the surfactant(s) (most suitably propylene glycol) at a concentration of from about 0.06 mg/mL to about 60 mg/mL, more suitably from about 0.6 mg/mL to about 30 mg/mL, more suitably from about 4 mg/mL to about 8 mg/mL. In an embodiment, the surfactant(s) is present at a concentration of about 6 mg/mL. In a particular embodiment, propylene glycol is present at a concentration of about 6 mg/mL. These values for the surfactant may suitably replace any values given herein in relation to a surfactant (e.g. in other embodiments), and these values, especially in relation to propylene glycol, may replaced corresponding values relating to polysorbate 20.

In some embodiments, the topical liquid composition is (substantially or entirely) free of surfactant(s).

Sugars

The topical liquid composition may comprise a sugar or sugar alcohol. In a particular embodiment, the sugar is or comprises glucose and/or sucrose. A sugar may be present instead of a tonicifer (e.g. sucrose may essentially act as a tonicifier). A sugar may be present instead of an amino acid (e.g. glucose may essentially act as a stabiliser).

Suitably, the topical liquid composition may comprise the sugar or sugar alcohol (most suitably either glucose or sucrose) at a concentration of from about 0.01 mg/mL to about 200 mg/mL, more suitably from about 1 mg/mL to about 100 mg/mL, more suitably from about 10 mg/mL to about 60 mg/mL. In an embodiment, the sugar or sugar alcohol (especially where it is glucose) is present at a concentration of about 20 mg/mL. In an embodiment, the sugar or sugar alcohol (especially where it is sucrose) is present at a concentration of about 50 mg/mL.

Diluent

The topical liquid compositions of the invention may include any one or more pharmaceutically acceptable diluents, or mixtures thereof. However, most suitably the topical liquid composition is an aqueous topical liquid composition. Most suitably the diluent is water, and suitably water alone. The water is suitably water for injection (WFI).

Suitably the diluent may constitute the balance of ingredients in any topical liquid composition, for instance so that the weight percentages total 100%. Suitably any concentrations given herein in relation to any component of the topical liquid composition represent concentrations of said component in (and suitably dissolved in) the diluent in admixture with any other components.

The topical liquid composition of the invention is suitably a solution, and is suitably (substantially or entirely) free of particulates or precipitates. The topical liquid composition is suitably (substantially or entirely) free of particulates having a particle size greater than or equal to 10 μm, suitably free of particulates having a particle size greater than or equal to 1 μm, suitably free of particulates having a particle size greater than or equal to 0.25 μm.

Stability Characteristics

The topical liquid compositions of the invention exhibit excellent stability over relatively long time periods at standard temperature and pressure (SATP, i.e. 25° C.), at low temperatures (e.g. 2-8° C.) and also elevated temperatures (e.g. 40° C.).

The concentration of the active ingredient (e.g. melatonin) within the topical liquid composition suitably remains (substantially) constant, or changes very little, after 20 weeks storage at 25° C., and suitably after 33 weeks storage at 25° C. Suitably, the concentration of the active ingredient varies (or decreases) by no more than 20% over such periods, suitably by no more than 10%, suitably by no more than 5%.

The concentration of the active ingredient (e.g. melatonin) within the topical liquid composition suitably remains (substantially) constant, or changes very little, after 1, 3, 4, 14, and/or 33 weeks storage at 40° C. Suitably, the concentration of the active ingredient varies (or decreases) by no more than 20% over such periods, suitably by no more than 10%, suitably by no more than 5%.

The concentration of the active ingredient (e.g. melatonin) within the topical liquid composition suitably remains (substantially) constant, or changes very little, after 33 weeks storage at 2-8° C. Suitably, the concentration of the active ingredient varies (or decreases) by no more than 10% over such periods, suitably by no more than 5%, suitably by no more than 1%.

The pH of the topical liquid composition suitably remains (substantially) constant, or changes very little, after 20 weeks storage at 25° C., and suitably after 33 weeks storage at 25° C. Suitably the pH varies by no more than 5% over such time periods, suitably by no more than 2%, suitably by no more than 1.5%, suitably by no more than 1.3%, The pH of the topical liquid composition suitably remains (substantially) constant, or changes very little, after 1, 3, 4, 14, and/or 33 weeks storage at 40° C. Suitably the pH varies by no more than 5% over such time periods, suitably by no more than 2%, suitably by no more than 1.5%, suitably by no more than 1.3%.

The pH of the topical liquid composition suitably remains (substantially) constant, or changes very little, after 33 weeks storage at 2-8° C. Suitably the pH varies by no more than 5% over such time periods, suitably by no more than 2%, suitably by no more than 1.5%, suitably by no more than 1.3%.

The osmolality of the topical liquid composition suitably remains (substantially) constant, or changes very little, after 20 weeks storage at 25° C., and suitably after 33 weeks storage at 25° C. Suitably the osmolality varies by no more than 10% over such time periods, suitably by no more than 5%, suitably by no more than 3%, suitably by no more than 2.5%, The osmolality of the topical liquid composition suitably remains (substantially) constant, or changes very little, after 4 and/or 33 weeks storage at 40° C. Suitably the osmolality varies by no more than 10% over such time periods, suitably by no more than 5%, suitably by no more than 4%, suitably by no more than 3.5%.

The osmolality of the topical liquid composition suitably remains (substantially) constant, or changes very little, after 33 weeks storage at 2-8° C. Suitably the osmolality varies by no more than 10% over such time periods, suitably by no more than 5%, suitably by no more than 4%, suitably by no more than 3.5%.

Specific Embodiments

In a particular embodiment, the topical liquid composition comprises melatonin (N-acetyl-5-methoxytryptamine) and/or an analog thereof, or a pharmaceutically acceptable salt or solvate thereof; a buffer system; and a combination of both arginine and methioinine.

In a particular embodiment, the topical liquid composition comprises:
  2-200 ng/mL melatonin (N-acetyl-5-methoxytryptamine) and/or an analog thereof, or a pharmaceutically acceptable salt or solvate thereof; and
  0.01-100 mM phosphate buffer system (suitably at a concentration of 0.00098-9.8 mg/mL in terms of phosphoric acid equivalents)
  one or more further components selected from:
    a first amino acid comprising at least one sulphur atom (suitably a divalent sulphur atom, such as a thiol or thioester), suitably selected from methionine and cysteine;
    a second amino acid that is free of any sulphur atoms;
    a tonicifier; and/or
    a non-ionic surfactant;
  water (suitably as the remaining balance by weight);
wherein the pH of the composition is pH 7-8.5, and the composition has an osmolality of 250-350 mOsm/kg.

In a particular embodiment, the topical liquid composition comprises:
  5-30 ng/mL melatonin (N-acetyl-5-methoxytryptamine) and/or an analog thereof, or a pharmaceutically acceptable salt or solvate thereof; and
  1-50 mM phosphate buffer system (suitably at a concentration of 0.098-4.9 mg/mL in terms of phosphoric acid equivalents);
  one or more further components selected from:
    a first amino acid comprising at least one sulphur atom (suitably a divalent sulphur atom, such as a thiol or thioester), suitably selected from methionine and cysteine;
    a second amino acid that is free of any sulphur atoms;
    a tonicifier; and/or
    a non-ionic surfactant;
  water (suitably as the remaining balance by weight);
wherein the pH of the composition is pH 7.5-7.9, and the composition has an osmolality of 280-330 mOsm/kg.

In a particular embodiment, the topical liquid composition comprises:
  15-25 ng/mL melatonin (N-acetyl-5-methoxytryptamine) and/or an analog thereof, or a pharmaceutically acceptable salt or solvate thereof; and
  5-15 mM phosphate buffer system (suitably at a concentration of 0.49-1.47 mg/mL in terms of phosphoric acid equivalents);
  one or more further components selected from:
    a first amino acid comprising at least one sulphur atom (suitably a divalent sulphur atom, such as a thiol or thioester), suitably selected from methionine and cysteine;

a second amino acid that is free of any sulphur atoms;
a tonicifier; and/or
a non-ionic surfactant;
water (suitably as the remaining balance by weight);
wherein the pH of the composition is pH 7.6-7.8, and the composition has an osmolality of 295-315 mOsm/kg.

In a particular embodiment, the topical liquid composition comprises:
2-200 ng/mL melatonin (N-acetyl-5-methoxytryptamine) and/or an analog thereof, or a pharmaceutically acceptable salt or solvate thereof; and
0.01-100 mM phosphate buffer system (suitably at a concentration of 0.00098-9.8 mg/mL in terms of phosphoric acid equivalents);
one or more further components selected from:
$1\times10^{-6}$ to 5 mg/mL methionine or cysteine;
0.0008-8 mg/mL arginine (suitably provided as about 0.001-10 mg/mL arginine.HCl);
1-100 mg/mL sodium chloride;
0.001-10 mg/mL polysorbate 20 or alternatively 0.1-100 mg/mL propylene glycol;
water (suitably as the remaining balance by weight);
wherein the pH of the composition is pH 7-8.5, and the composition has an osmolality of 250-350 mOsm/kg.

In a particular embodiment, the topical liquid composition comprises:
5-30 ng/mL melatonin (N-acetyl-5-methoxytryptamine) and/or an analog thereof, or a pharmaceutically acceptable salt or solvate thereof; and
1-50 mM phosphate buffer system (suitably at a concentration of 0.098-4.9 mg/mL in terms of phosphoric acid equivalents);
one or more further components selected from:
0.001-1.0 mg/mL methionine or cysteine;
0.008-0.8 mg/mL arginine (suitably provided as about 0.01-1.0 mg/mL arginine.HCl);
2-30 mg/mL sodium chloride; and/or
0.01-1.0 mg/mL polysorbate 20 or alternatively 1-10 mg/mL propylene glycol;
water (suitably as the remaining balance by weight);
wherein the pH of the composition is pH 7.5-7.9, and the composition has an osmolality of 280-330 mOsm/kg.

In a particular embodiment, the topical liquid composition comprises:
15-25 ng/mL melatonin (N-acetyl-5-methoxytryptamine) and/or an analog thereof, or a pharmaceutically acceptable salt or solvate thereof; and
5-15 mM phosphate buffer system (suitably at a concentration of 0.49-1.47 mg/mL in terms of phosphoric acid equivalents);
one or more further components selected from:
0.005-0.015 mg/mL methionine or cysteine;
0.04-0.4 mg/mL arginine (suitably provided as about 0.05-0.5 mg/mL arginine.HCl);
5-12 mg/mL sodium chloride; and/or
0.025-0.075 mg/mL polysorbate 20 or alternatively 4-8 mg/mL propylene glycol;
water (suitably as the remaining balance by weight);
wherein the pH of the composition is pH 7.6-7.8, and the composition has an osmolality of 295-315 mOsm/kg.

In a particular embodiment, the topical liquid composition comprises:
2-200 ng/mL melatonin (N-acetyl-5-methoxytryptamine) and/or an analog thereof, or a pharmaceutically acceptable salt or solvate thereof; and
0.01-100 mM phosphate buffer system (suitably at a concentration of 0.00098-9.8 mg/mL in terms of phosphoric acid equivalents);
1-100 mg/mL tonicifier;
water (suitably as the remaining balance by weight);
wherein the pH of the composition is pH 7-8.5.

In a particular embodiment, the topical liquid composition comprises:
2-200 ng/mL melatonin (N-acetyl-5-methoxytryptamine) and/or an analog thereof, or a pharmaceutically acceptable salt or solvate thereof;
0.01-100 mM phosphate buffer system (suitably at a concentration of 0.00098-9.8 mg/mL in terms of phosphoric acid equivalents);
0.01-100 mM histidine buffer system;
1-100 mg/mL tonicifier;
water (suitably as the remaining balance by weight);
wherein the pH of the composition is pH 7-8.5.

In a particular embodiment, the topical liquid composition comprises:
5-30 ng/mL melatonin (N-acetyl-5-methoxytryptamine) and/or an analog thereof, or a pharmaceutically acceptable salt or solvate thereof; and
1-50 mM phosphate buffer system (suitably at a concentration of 0.098-4.9 mg/mL in terms of phosphoric acid equivalents);
2-30 mg/mL tonicifier;
water (suitably as the remaining balance by weight);
wherein the pH of the composition is pH 7.5-7.9.

In a particular embodiment, the topical liquid composition comprises:
5-30 ng/mL melatonin (N-acetyl-5-methoxytryptamine) and/or an analog thereof, or a pharmaceutically acceptable salt or solvate thereof; and
1-50 mM phosphate buffer system (suitably at a concentration of 0.098-4.9 mg/mL in terms of phosphoric acid equivalents);
1-50 mM histidine buffer system;
2-30 mg/mL tonicifier;
water (suitably as the remaining balance by weight);
wherein the pH of the composition is pH 7.5-7.9.

In a particular embodiment, the topical liquid composition comprises:
15-25 ng/mL melatonin (N-acetyl-5-methoxytryptamine) and/or an analog thereof, or a pharmaceutically acceptable salt or solvate thereof; and
5-15 mM phosphate buffer system (suitably at a concentration of 0.49-1.47 mg/mL in terms of phosphoric acid equivalents);
5-12 mg/mL tonicifier;
water (suitably as the remaining balance by weight);
wherein the pH of the composition is pH 7.6-7.8.

In a particular embodiment, the topical liquid composition comprises:
15-25 ng/mL melatonin (N-acetyl-5-methoxytryptamine) and/or an analog thereof, or a pharmaceutically acceptable salt or solvate thereof; and
5-15 mM phosphate buffer system (suitably at a concentration of 0.49-1.47 mg/mL in terms of phosphoric acid equivalents);
5-15 mM histidine buffer system;
5-12 mg/mL tonicifier;
water (suitably as the remaining balance by weight);
wherein the pH of the composition is pH 7.6-7.8.

In a particular embodiment, the topical liquid composition comprises:

2-200 ng/mL melatonin (N-acetyl-5-methoxytryptamine) and/or an analog thereof, or a pharmaceutically acceptable salt or solvate thereof; and 0.01-100 mM buffer system (suitably at a concentration of 0.00098-9.8 mg/mL in terms of conjugate acid equivalents);

$1\times10^{-6}$ to 5 mg/mL first amino acid comprising at least one sulphur atom (suitably a divalent sulphur atom, such as a thiol or thioester);

water (suitably as the remaining balance by weight);

wherein the pH of the composition is pH 7-8.5, and the composition has an osmolality of 250-350 mOsm/kg.

In a particular embodiment, the topical liquid composition comprises:

5-30 ng/mL melatonin (N-acetyl-5-methoxytryptamine) and/or an analog thereof, or a pharmaceutically acceptable salt or solvate thereof; and 1-50 mM buffer system (suitably at a concentration of 0.098-4.9 mg/mL in terms of conjugate acid equivalents);

0.001-1.0 mg/mL first amino acid comprising at least one sulphur atom (suitably a divalent sulphur atom, such as a thiol or thioester);

water (suitably as the remaining balance by weight);

wherein the pH of the composition is pH 7.5-7.9, and the composition has an osmolality of 280-330 mOsm/kg.

In a particular embodiment, the topical liquid composition comprises:

15-25 ng/mL melatonin (N-acetyl-5-methoxytryptamine) and/or an analog thereof, or a pharmaceutically acceptable salt or solvate thereof; and 5-15 mM buffer system (suitably at a concentration of 0.49-1.47 mg/mL in terms of conjugate acid equivalents);

0.005-0.015 mg/mL first amino acid comprising at least one sulphur atom (suitably a divalent sulphur atom, such as a thiol or thioester);

water (suitably as the remaining balance by weight);

wherein the pH of the composition is pH 7.6-7.8, and the composition has an osmolality of 295-320 mOsm/kg.

In a particular embodiment, the topical liquid composition comprises:

2-200 ng/mL melatonin (N-acetyl-5-methoxytryptamine) and/or an analog thereof, or a pharmaceutically acceptable salt or solvate thereof; and 0.01-100 mM phosphate buffer system (suitably at a concentration of 0.00098-9.8 mg/mL in terms of phosphoric acid equivalents);

$1\times10^{-6}$ to 5 mg/mL first amino acid comprising at least one sulphur atom (suitably a divalent sulphur atom, such as a thiol or thioester), suitably selected from methionine and/or cysteine;

water (suitably as the remaining balance by weight);

wherein the pH of the composition is pH 7-8.5, and the composition has an osmolality of 250-350 mOsm/kg.

In a particular embodiment, the topical liquid composition comprises:

5-30 ng/mL melatonin (N-acetyl-5-methoxytryptamine) and/or an analog thereof, or a pharmaceutically acceptable salt or solvate thereof; and 1-50 mM phosphate buffer system (suitably at a concentration of 0.098-4.9 mg/mL in terms of phosphoric acid equivalents);

0.001-1.0 mg/mL first amino acid comprising at least one sulphur atom (suitably a divalent sulphur atom, such as a thiol or thioester), suitably selected from methionine and/or cysteine;

water (suitably as the remaining balance by weight);

wherein the pH of the composition is pH 7.5-7.9, and the composition has an osmolality of 280-330 mOsm/kg.

In a particular embodiment, the topical liquid composition comprises:

2-200 ng/mL melatonin (N-acetyl-5-methoxytryptamine) and/or an analog thereof, or a pharmaceutically acceptable salt or solvate thereof; and 0.01-100 mM phosphate buffer system (suitably at a concentration of 0.00098-9.8 mg/mL in terms of phosphoric acid equivalents);

0.01-100 mM histidine buffer system;

water (suitably as the remaining balance by weight);

wherein the pH of the composition is pH 7-8.5, and the composition has an osmolality of 250-350 mOsm/kg.

In a particular embodiment, the topical liquid composition comprises:

15-25 ng/mL melatonin (N-acetyl-5-methoxytryptamine) and/or an analog thereof, or a pharmaceutically acceptable salt or solvate thereof; and 5-15 mM phosphate buffer system (suitably at a concentration of 0.49-1.47 mg/mL in terms of phosphoric acid equivalents);

0.005-0.015 mg/mL first amino acid comprising at least one sulphur atom (suitably a divalent sulphur atom, such as a thiol or thioester), suitably selected from methionine and/or cysteine;

water (suitably as the remaining balance by weight);

wherein the pH of the composition is pH 7.6-7.8, and the composition has an osmolality of 295-315 mOsm/kg.

In a particular embodiment, the topical liquid composition comprises:

15-25 ng/mL melatonin (N-acetyl-5-methoxytryptamine) and/or an analog thereof, or a pharmaceutically acceptable salt or solvate thereof; and 5-15 mM phosphate buffer system (suitably at a concentration of 0.49-1.47 mg/mL in terms of phosphoric acid equivalents);

5-15 mM histidine buffer system;

water (suitably as the remaining balance by weight);

wherein the pH of the composition is pH 7.6-7.8, and the composition has an osmolality of 295-315 mOsm/kg.

In a particular embodiment, the topical liquid composition comprises:

2-200 ng/mL melatonin (N-acetyl-5-methoxytryptamine) and/or an analog thereof, or a pharmaceutically acceptable salt or solvate thereof; and 0.01-100 mM buffer system (suitably at a concentration of 0.00098-9.8 mg/mL in terms of conjugate acid equivalents);

$1\times10^{-6}$ to 5 mg/mL first amino acid comprising at least one sulphur atom (suitably a divalent sulphur atom, such as a thiol or thioester);

1-100 mg/mL tonicifier;

water (suitably as the remaining balance by weight);

wherein the pH of the composition is pH 7-8.5, and the composition has an osmolality of 250-350 mOsm/kg.

In a particular embodiment, the topical liquid composition comprises:

5-30 ng/mL melatonin (N-acetyl-5-methoxytryptamine) and/or an analog thereof, or a pharmaceutically acceptable salt or solvate thereof; and 1-50 mM buffer system (suitably at a concentration of 0.098-4.9 mg/mL in terms of conjugate acid equivalents);
0.001-1.0 mg/mL first amino acid comprising at least one sulphur atom (suitably a divalent sulphur atom, such as a thiol or thioester);
2-30 mg/mL tonicifier;
water (suitably as the remaining balance by weight);

wherein the pH of the composition is pH 7.5-7.9, and the composition has an osmolality of 280-330 mOsm/kg.

In a particular embodiment, the topical liquid composition comprises:
15-25 ng/mL melatonin (N-acetyl-5-methoxytryptamine) and/or an analog thereof, or a pharmaceutically acceptable salt or solvate thereof; and
5-15 mM buffer system (suitably at a concentration of 0.49-1.47 mg/mL in terms of conjugate acid equivalents);
0.005-0.015 mg/mL first amino acid comprising at least one sulphur atom (suitably a divalent sulphur atom, such as a thiol or thioester);
5-12 mg/mL tonicifier;
water (suitably as the remaining balance by weight);

wherein the pH of the composition is pH 7.6-7.8, and the composition has an osmolality of 295-315 mOsm/kg.

In a particular embodiment, the topical liquid composition comprises:
20 ng/mL melatonin (N-acetyl-5-methoxytryptamine) and/or an analog thereof, or a pharmaceutically acceptable salt or solvate thereof; and
10 mM buffer system (suitably at a concentration of 0.98 mg/mL in terms of conjugate acid equivalents);
0.01 mg/mL first amino acid comprising at least one sulphur atom (suitably a divalent sulphur atom, such as a thiol or thioester);
9 mg/mL tonicifier;
water (suitably as the remaining balance by weight);

wherein the pH of the composition is pH 7.7.

In a particular embodiment, the topical liquid composition comprises:
2-200 ng/mL melatonin (N-acetyl-5-methoxytryptamine) and/or an analog thereof, or a pharmaceutically acceptable salt or solvate thereof; and
0.01-100 mM buffer system;
$1 \times 10^{-6}$ to 5 mg/mL first amino acid comprising at least one sulphur atom (suitably a divalent sulphur atom, such as a thiol or thioester);
0.0008-8 mg/mL second amino acid that is free of any sulphur atoms;
1-100 mg/mL tonicifier;
0.001-10 mg/mL non-ionic surfactant;
water (suitably as the remaining balance by weight);

wherein the pH of the composition is pH 7-8.5, and the composition has an osmolality of 250-350 mOsm/kg.

In a particular embodiment, the topical liquid composition comprises:
5-30 ng/mL melatonin (N-acetyl-5-methoxytryptamine) and/or an analog thereof, or a pharmaceutically acceptable salt or solvate thereof; and
1-50 mM buffer system;
0.001-1.0 mg/mL first amino acid comprising at least one sulphur atom (suitably a divalent sulphur atom, such as a thiol or thioester);
0.008-0.8 mg/mL second amino acid that is free of any sulphur atoms;
2-30 mg/mL tonicifier;
0.01-1.0 mg/mL non-ionic surfactant;
water (suitably as the remaining balance by weight);

wherein the pH of the composition is pH 7.5-7.9, and the composition has an osmolality of 280-330 mOsm/kg.

In a particular embodiment, the topical liquid composition comprises:
15-25 ng/mL melatonin (N-acetyl-5-methoxytryptamine) and/or an analog thereof, or a pharmaceutically acceptable salt or solvate thereof; and
5-15 mM buffer system;
0.005-0.015 mg/mL first amino acid comprising at least one sulphur atom (suitably a divalent sulphur atom, such as a thiol or thioester);
0.04-0.4 mg/mL second amino acid that is free of any sulphur atoms;
5-12 mg/mL tonicifier;
0.025-0.075 mg/mL non-ionic surfactant;
water (suitably as the remaining balance by weight);

wherein the pH of the composition is pH 7.6-7.8, and the composition has an osmolality of 295-320 mOsm/kg.

In a particular embodiment, the topical liquid composition comprises:
20 ng/mL melatonin (N-acetyl-5-methoxytryptamine) and/or an analog thereof, or a pharmaceutically acceptable salt or solvate thereof; and
10 mM buffer system;
0.01 mg/mL first amino acid comprising at least one sulphur atom (suitably a divalent sulphur atom, such as a thiol or thioester);
0.082-0.084 mg/mL second amino acid that is free of any sulphur atoms;
9 mg/mL tonicifier;
0.05 mg/mL non-ionic surfactant;
water (suitably as the remaining balance by weight);

wherein the pH of the composition is pH 7.7.

In a particular embodiment, the topical liquid composition comprises:
2-200 ng/mL melatonin (N-acetyl-5-methoxytryptamine) and/or an analog thereof, or a pharmaceutically acceptable salt or solvate thereof; and
0.01-100 mM phosphate buffer system;
$1 \times 10^{-6}$ to 5 mg/mL methionine;
0.0008-8 mg/mL arginine (suitably provided as about 0.001-10 mg/mL arginine.HCl);
1-100 mg/mL sodium chloride;
0.001-10 mg/mL polysorbate 20;
water (suitably as the remaining balance by weight);

wherein the pH of the composition is pH 7-8.5, and the composition has an osmolality of 250-350 mOsm/kg.

In a particular embodiment, the topical liquid composition comprises:
2-200 ng/mL melatonin (N-acetyl-5-methoxytryptamine) and/or an analog thereof, or a pharmaceutically acceptable salt or solvate thereof; and
0.01-100 mM phosphate buffer system;
0.01-100 mM histidine buffer system;
0.0008-8 mg/mL arginine (suitably provided as about 0.001-10 mg/mL arginine.HCl);
1-100 mg/mL sodium chloride;
0.001-10 mg/mL polysorbate 20;
water (suitably as the remaining balance by weight);

wherein the pH of the composition is pH 7-8.5, and the composition has an osmolality of 250-350 mOsm/kg.

In a particular embodiment, the topical liquid composition comprises:
5-30 ng/mL melatonin (N-acetyl-5-methoxytryptamine) and/or an analog thereof, or a pharmaceutically acceptable salt or solvate thereof; and 1-50 mM phosphate buffer system;
0.001-1.0 mg/mL methionine;
0.008-0.8 mg/mL arginine (suitably provided as about 0.01-1.0 mg/mL arginine.HCl);
2-30 mg/mL sodium chloride;
0.01-1.0 mg/mL polysorbate 20;
water (suitably as the remaining balance by weight);
wherein the pH of the composition is pH 7.5-7.9, and the composition has an osmolality of 280-330 mOsm/kg.

In a particular embodiment, the topical liquid composition comprises:
  5-30 ng/mL melatonin (N-acetyl-5-methoxytryptamine) and/or an analog thereof, or a pharmaceutically acceptable salt or solvate thereof; and
  1-50 mM phosphate buffer system;
  1-50 mM histidine buffer system;
  0.008-0.8 mg/mL arginine (suitably provided as about 0.01-1.0 mg/mL arginine.HCl);
  2-30 mg/mL sodium chloride;
  0.01-1.0 mg/mL polysorbate 20;
  water (suitably as the remaining balance by weight);
wherein the pH of the composition is pH 7.5-7.9, and the composition has an osmolality of 280-330 mOsm/kg.

In a particular embodiment, the topical liquid composition comprises:
  15-25 ng/mL melatonin (N-acetyl-5-methoxytryptamine) and/or an analog thereof, or a pharmaceutically acceptable salt or solvate thereof; and
  5-15 mM phosphate buffer system;
  0.005-0.015 mg/mL methionine;
  0.04-0.4 mg/mL arginine (suitably provided as about 0.05-0.5 mg/mL arginine.HCl);
  5-12 mg/mL sodium chloride;
  0.025-0.075 mg/mL polysorbate 20;
  water (suitably as the remaining balance by weight);
wherein the pH of the composition is pH 7.6-7.8, and the composition has an osmolality of 295-320 mOsm/kg.

In a particular embodiment, the topical liquid composition comprises:
  15-25 ng/mL melatonin (N-acetyl-5-methoxytryptamine) and/or an analog thereof, or a pharmaceutically acceptable salt or solvate thereof; and
  5-15 mM phosphate buffer system;
  5-15 mM histidine buffer system;
  0.04-0.4 mg/mL arginine (suitably provided as about 0.05-0.5 mg/mL arginine.HCl);
  5-12 mg/mL sodium chloride;
  0.025-0.075 mg/mL polysorbate 20;
  water (suitably as the remaining balance by weight);
wherein the pH of the composition is pH 7.6-7.8, and the composition has an osmolality of 295-320 mOsm/kg.

In a particular embodiment, the topical liquid composition comprises:
  20 ng/mL melatonin (N-acetyl-5-methoxytryptamine) and/or an analog thereof, or a pharmaceutically acceptable salt or solvate thereof; and
  10 mM phosphate buffer system;
  0.01 mg/mL methionine;
  0.082-0.084 mg/mL arginine (suitably provided as 0.1 mg/mL arginine.HCl);
  9 mg/mL sodium chloride;
  0.05 mg/mL polysorbate 20;
  water (suitably as the remaining balance by weight);
wherein the pH of the composition is pH 7.7.

In a particular embodiment, the topical liquid composition comprises:
  20 ng/mL melatonin (N-acetyl-5-methoxytryptamine) and/or an analog thereof, or a pharmaceutically acceptable salt or solvate thereof; and
  10 mM phosphate buffer system;
  10 mM histidine buffer system;
  0.082-0.084 mg/mL arginine (suitably provided as 0.1 mg/mL arginine.HCl);
  9 mg/mL sodium chloride;
  0.05 mg/mL polysorbate 20;
  water (suitably as the remaining balance by weight);
wherein the pH of the composition is pH 7.7.

Any of the aforementioned embodiments, or any embodiments defined anywhere herein, may comprise a histidine buffer system, optionally alternative to or in addition to another buffer, such as a phosphate buffer, though most suitably any histidine buffer is in addition to a phosphate buffer. The aforementioned embodiments may comprise a histidine buffer, suitably in any of the amounts stipulated hereinbefore in relation to a buffer system, though suitably such amounts of histidine buffer are in addition to a stipulated amount of another buffer system (e.g. phosphate buffer), such that the total amount of the buffer system is the combined total of the histidine buffer system and another buffer system (e.g. phosphate buffer system). For example, in an embodiment, the composition comprises 10 mM phosphate buffer system and also 10 mM histidine buffer system, so the total amount of buffer system is 20 mM.

All of the aforementioned embodiments may be given as relative compositions rather than absolute compositions. As such, the weight concentration values in respect of the plurality of ingredients may be replaced by relative weight concentration values (e.g. parts by weight, pbw). This is reasonable since the topical liquid compositions may be desirable stored and/or transported at higher concentrations, and duly diluted prior to use.

Preparation of Topical Liquid Composition

The present invention provides a method of manufacturing a topical liquid composition, suitably as defined herein. The method suitably comprises mixing together, in any particular order deemed appropriate, any relevant components required to form a topical liquid composition as defined herein. The skilled person may refer to the Examples or techniques well known in the art for forming topical liquid compositions. Different embodiments will suitably require different combinations of components to be mixed, potentially in different amounts. The skilled person can readily deduce such combinations and amounts by reference to the foregoing disclosure relating to the topical liquid composition.

Suitably the method involves mixing together the relevant components suitably, in a diluent (e.g. water), suitably so that all of the components are (substantially or entirely) dissolved in the diluent.

The method may involve first preparing a one or more pre-mixtures (or pre-solutions) of each, some or all components (optionally with some or all of the diluent), before said pre-mixture(s) or pre-solution(s) are then mixed together, optionally along with any components not provided as a pre-mixture or pre-solution within a diluents, to ultimately form either the topical liquid composition or a topical liquid precursor composition (which may then undergo further processing to produce the topical liquid composition).

Suitably, the method involves forming a buffer system, suitably a buffer system comprising a buffering agent as defined herein. The buffer system is suitably formed in a pre-mixture prior to mixing with the one or more other components, though the buffer system may optionally be formed in the presence of one or more of the other components. The buffer system may be formed as previously defined herein, though once the buffer system is mixed with all other components (this may represent a topical liquid precursor composition), the pH may thereafter be adjusted or fine-tuned to an appropriate pH values (e.g. through the addition of a strong acid and/or strong base).

In certain embodiments, the buffering agent and/or buffer system is pre-formed as a separate mixture, and the buffer system is transferred to a topical liquid precursor composition (comprising some or all components save for the buffering agent and/or buffer system) via buffer exchange (e.g. using diafiltration until the relevant concentrations or osmolality is reached). Additional excipients may be added thereafter if necessary in order to produce the final topical liquid composition. The pH may be adjusted once or before all the components are present.

Any, some, or all components may be pre-dissolved or pre-mixed with a diluent prior to mixing with other components.

The final topical liquid composition may be filtered, suitably to remove particulate matter. Suitably filtration is through filters sized at or below 1 μm, suitably at 0.22 μm. Suitably, filtration is through either PES filteres or PVDF filters, suitably with 0.22 μm PES filters.

The present invention also provides a topical liquid composition obtainable by, obtained by, or directly obtained by the method of manufacture herein described.

Package or Medical Device

The topical liquid compositions of the invention may be incorporated into a package or medical device, for example, a medical device such as that disclosed in WO2013/178587 (MAXIA et al). Since uterine washing is a relatively non-invasive practice that allows restoration of the uterine physiological conditions through mechanical removal of secretes, which may alter the implantation conditions, the invention has as a further object a medical device for uterine washing comprising a sterile container pre-filled or to be filled with a composition as defined herein. The present invention therefore provides a package or medical device, comprising a sterile container pre-filled or configured for filling with a topical liquid composition as defined herein.

The sterile container is suitably selected from a syringe, dispenser, cartridge, or self-injection pen.

The topical liquid compositions of the invention may be formulated as gel suitable for uterine administration, more precisely for in situ administration in the uterine cavity, preferably with a medical device being an intrauterine "T shaped" device. It is also possible to foresee controlled release gel formulations for mucosal administration.

In some embodiments, the device or package may be filled immediately prior to use with the topical liquid composition. In some embodiments, the topical liquid composition may be formed within the device or package. However, an advantage of the formulations of the invention is that they are sufficiently stable to permit devices or packages to be used which were filled many weeks prior to their ultimate use.

In some embodiments of the invention, the package or medical device may further comprise a catheter (suitably a sterile flexible catheter), preferably with a single terminal hole. A catheter may be suitably used to deliver the topical liquid composition to the site of topical administration (e.g. the uterus).

Kit of Parts

The present invention provides a kit of parts comprising a medical device (without the topical liquid composition incorporated therein), a topical liquid composition as defined herein (optionally contained in a separate package or container), and optionally a set of instructions with directions regarding the administration (e.g. topical) of the topical liquid composition. The user may then fill the medical device with the topical liquid composition (which may be provided in a vial or ampoule or such like) prior to administration.

Uses of Pharmaceutical Liquid Composition and Methods of Treatment

The present invention provides a topical liquid composition, as defined herein, for use in therapy. The therapy in question is suitably fertility treatment (or the treatment of infertility). As such, the topical liquid composition may be used in assisted reproduction treatments, such as in vitro fertilisation treatments.

In particular, the topical liquid compositions of the invention may be used to treat, inhibit, or prevent embryonic implantation failure (especially during assisted reproduction treatments). Accordingly, the topical liquid compositions of the invention may be used in promoting embryonic implantation, improving embryonic implantation, inhibiting and/or preventing embryonic implantation failure, reducing the probability of embryonic implantation failure, facilitating assisted reproduction, promoting uterine receptivity to embryonic implantation, and/or treating a uterus.

The topical liquid compositions of the invention are generally utilised in a method of washing and/or irrigating a uterus and/or endometrium (suitably to prepare the uterus/endometrium for the transfer of embryos to promote implantation or otherwise inhibit implantation failure), which method involves topically administering the topical liquid composition as defined herein to the uterus and/or endometrium. Such washing/irrigation methods suitably facilitate implantation of an embryo within a uterus through being part of a method comprising:

(i) washing and/or irrigating the uterus and/or endometrium with a topical liquid composition as defined herein;
(ii) transferring an embryo (e.g. one form via IVF) to the uterus (suitably after, suitably one or more days after, step (i)); and
(iii) allowing the embryo to become implanted within the uterus (and optionally monitoring the progress of implantation and/or pregnancy thereafter).

WO2013/178587 (MAXIA et al), which is hereby incorporated by reference, describes the process and variants thereof is more detailed.

Suitably, the compositions, packages, and medical devices defined herein are for use in assisted reproduction, in particular in the inhibition and/or prevention of embryonic implantation failure into the uterus. Such compositions, packages, and medical devices are suitably for use in the medical or veterinary field. Suitably such compositions, packages, and medical devices are for topical administration, suitably into the uterus. The compositions, packages, and medical devices are suitably for use in assisting reproduction in a mammalian subject (suitably a female mammalian subject), suitably in a subject in need of such treatment, most suitably for use in assisting reproduction in a human subject. Suitably, topical administration of the compositions, packages, and medical devices involves topical administration of an (therapeutically) effective amount of the composition.

In a particular embodiment, assisted reproduction comprises in vitro fertilization (IVF) and embryo transfer (e.g. FIVET). Such a treatment process generally involves:

(i) Obtaining complementary gametes (e.g. suitably obtaining one or more ova from a female, and a plurality of sperms from a male);

(ii) Co-incubating the complementary gametes within a suitable culture medium to facilitate fertilisation to thereby produce one or more zygotes;
(iii) Culturing the one or more zygotes within a suitable growth medium to form one or more embryos;
(iv) Optionally culturing the one or more embryos in an embryo culture medium until a cleavage or blastocyst stage;
(v) Optionally selecting one or more of the one or more embryos;
(vi) transferring to a subject's (or patient's) uterus (suitably through a thin, plastic catheter, which goes through her vagina and cervix) one or more (of the optionally selected) embryos;
(vii) allowing embryonic implantation to take place and pregnancy to ensue.

The uterus and/or endometrium to which the embryo(s) are to be transferred in step (vi) may be suitably washed or irrigated beforehand with a topical liquid composition of the invention. Such washings (preferably performed with the aid of a catheter), especially when performed 2-5 days before embryo transfer, preferably three days before, promote embryonic implantation and/or inhibit embryonic implantation failure. In some embodiments, a topical liquid composition of the invention may be used in conjunction with another composition (including another washing composition) during uterine washing/irrigation. In some embodiments, such other compositions may be pre-mixed with the topical liquid composition of the invention prior to their simultaneous topical administration. Alternatively, the respective compositions may be administered in sequence. WO2013/178587 (MAXIA et al) describes various combinations used, including topical liquid compositions being used with culture mediums. However, the topical liquid compositions of the invention are ultimately used, the topical liquid compositions themselves are extremely advantageous in terms of their stability, meaning they can be provided as defined herein and used at a much later stage in a suitable treatment method.

EXAMPLES

The invention is now described in detail by way of the following non-limiting Examples.

Materials and Equipment

The following melatonin solutions were used in the ensuing Examples:
Melatonin Bulk solution:
    packaged in glass bottle;
    packaged in plastic bag.
Melatonin 20 ng/ml solutions containing different excipients/antioxidants packaged in glass vials (see Table 1 for a detailed description of the compositions);
Concentrated Melatonin ("5×") solutions (100 ng/ml) containing different excipients/antioxidants packaged in glass vials (see Table 2 for a detailed description of the compositions).

Samples of each of the solutions above described were stored for different periods at 2-8° C., 25° C. and 40° C. and subjected to the following tests, according to the experimental setup described in detail below.

HPLC determination of Melatonin content;
Osmolality
pH

TABLE 1

| Melatonin 20 ng/ml solutions (Candidate 0-9) | | | | |
|---|---|---|---|---|
| Candidate#0 | Candidate#1 | Candidate#2 | Candidate#3 | Candidate#4 |
| 10 mM phosphate buffer melatonin (20 ng/mL) WFI q.b to final weigh — — — | 10 mM phosphate buffer (0.1 mg/mL) L-Arginine HCl (9 mg/mL) NaCl (0.05 mg/mL) Polysorbate 20 melatonin (20 ng/mL) WFI q.b to final weigh | 10 mM phosphate buffer (0.01 mg/mL) L-methionine (0.1 mg/mL) L-Arginine HCl (9 mg/mL) NaCl (0.05 mg/mL) Polysorbate 20 melatonin (20 ng/mL) WFI q.b to final weigh | 10 mM phosphate buffer (0.1 mg/mL) L-Arginine HCl (9 mg/mL) NaCl (0.05 mg/mL) Polysorbate 20 melatonin (20 ng/mL) WFI q.b to final weigh | 10 mM phosphate buffer (13 ng/mL) L-methionine (0.1 mg/mL) L-Arginine HCl (9 mg/mL) NaCl (0.05 mg/mL) Polysorbate 20 melatonin (20 ng/mL) WFI q.b to final weigh |
| Candidate#5 | Candidate#6 | Candidate#7 | Candidate#8 | Candidate#9 |
| 10 mM phosphate buffer (0.01 mg/mL) L-cystein HCl × H2O (0.1 mg/mL) L-Arginine HCl (9 mg/mL) NaCl (0.05 mg/mL) Polysorbate 20 melatonin (20 ng/mL) WFI q.b to final weigh | 10 mM phosphate buffer (0.01 mg/mL) L-methionine (0.1 mg/mL) L-Arginine HCl (7 mg/mL) NaCl (6 mg/mL) propylen glycol melatonin (20 ng/mL) WFI q.b to final weigh | 10 mM phosphate buffer (0.01 mg/mL) L-methionine (8 mg/mL) L-glycine (6 mg/mL) NaCl melatonin (20 ng/mL) WFI q.b to final weigh | 10 mM phosphate buffer (20 mg/mL) glucose (6 mg/mL) NaCl melatonin (20 ng/mL) — WFI q.b to final weigh | 10 mM phosphate buffer (0.01 mg/mL) L-methionine (50 mg/mL) sucrose (0.05 mg/mL) Polysorbate 20 melatonin (20 ng/mL) WFI q.b to final weigh |

TABLE 2

Melatonin "5x" solutions (Candidate 0-9 "5x")

| Candidate#0 "5x" | Candidate#1 "5x" | Candidate#2 "5x" | Candidate#3 "5x" | Candidate#4 "5x" |
|---|---|---|---|---|
| 50 mM phosphate buffer melatonin (100 ng/mL) WFI q.b to final weigh — — — — | 50 mM phosphate buffer (0.5 mg/mL) L-Arginine HCl (45 mg/mL) NaCl (0.25 mg/mL) Polysorbate 20 melatonin (100 ng/mL) WFI q.b to final weigh — | 50 mM phosphate buffer (0.05 mg/mL) L-methionine (0.5 mg/mL) L-Arginine HCl (45 mg/mL) NaCl (0.25 mg/mL) Polysorbate 20 melatonin (100 ng/mL) WFI q.b to final weigh | 50 mM hystidinate buffer (0.05 mg/mL) L-methionine (0.5 mg/mL) L-Arginine HCl (45 mg/mL) NaCl (0.25 mg/mL) Polysorbate 20 melatonin (100 ng/mL) WFI q.b to final weigh | 50 mM phosphate buffer (65 ng/mL) L-methionine (0.5 mg/mL) L-Arginine HCl (45 mg/mL) NaCl (0.25 mg/mL) Polysorbate 20 melatonin (100 ng/mL) WFI q.b to final weigh |

| Candidate#5 "5x" | Candidate#6 "5x" | Candidate#7 "5x" | Candidate#8 "5x" | Candidate#9 "5x" |
|---|---|---|---|---|
| 50 mM phosphate buffer (0.05 mg/mL) L-cystein HCl × H2O (0.5 mg/mL) L-Arginine HCl (45 mg/mL) NaCl (0.25 mg/mL) Polysorbate 20 melatonin (100 ng/mL) WFI q.b to final weigh | 50 mM phosphate buffer (0.05 mg/mL) L-methionine (0.5 mg/mL) L-Arginine HCl (35 mg/mL) NaCl (30 mg/mL) propylen glycol melatonin (100 ng/mL) WFI q.b to final weigh | 50 mM phosphate buffer (0.05 mg/mL) L-methionine (40 mg/mL) L-glycine (30 mg/mL) NaCl melatonin (100 ng/mL) WFI q.b to final weigh — | 50 mM phosphate buffer (100 mg/mL) glucose (30 mg/mL) NaCl melatonin (100 ng/mL) — WFI q.b to final weigh — | 50 mM phosphate buffer (0.05 mg/mL) L-methionine (250 mg/mL) sucrose (0.25 mg/mL) Polysorbate 20 melatonin (100 ng/mL) WFI q.b to final weigh — |

Preparation of Melatonin Solutions

Bulk melatonin solutions, and samples thereof, were prepared according to Example 1 below, except that the filtered solution was divided into two portions, and packaged respectively into i) an amber glass bottle; and ii) a Millipore Mobius Silver 5 L bag.

Candidate solutions 0-9 were prepared according to the procedures set forth in Examples 0 to 9. Additional analysis was carried out on the unfiltered sample.

Concentrated (5x) candidate solutions 0-9 were also prepared according to the procedures set forth in Examples 0 to 9, adjusting the final concentration to above 5x that of the nominal sample, except Candidate 3 (5x) which contains also L-methionine.

Sample Storage and Analysis

Bulk melatonin solutions were stored at room temperature, protected from light, and sampled according to Table 3.

Candidate Solutions 0-9 were all stored in climatic chambers at 2-8° C., 25° C. and 40° C. Sampling was carried out according to Table 4, Table 5 and Table 6.

TABLE 4

Sampling points for Candidate Solutions at 2-8° C.

| Candidate Solutions | Storage (Weeks) | |
|---|---|---|
| (2-8° C.) | 0 | 33 |
| Melatonin (ng/ml) | ✓ | ✓ |
| Osmolality | ✓ | ✓ |
| pH | ✓ | ✓ |

TABLE 3

Sampling points for Bulk Solutions

| Bulk Solutions | Storage (Days) | | | | |
|---|---|---|---|---|---|
| (Room Temp) | 1 | 3 | 7 | 25 | 42 |
| Melatonin (ng/ml) | ✓ | ✓ | ✓ | ✓ | ✓ |
| Osmolality | ✓ | ✓ | ✓ | ✓ | ✓ |
| pH | — | — | — | — | ✓ |

TABLE 5

Sampling points for Candidate Solutions at 25° C.

| Candidate Solutions | Unfiltered | Storage (Weeks) | | |
|---|---|---|---|---|
| (25° C.) | Sample | 0 | 20 | 33 |
| Melatonin (ng/ml) | ✓ | ✓ | ✓ | ✓ |
| Osmolality | — | ✓ | ✓ | ✓ |
| pH | — | ✓ | ✓ | ✓ |

TABLE 6

Sampling points for Candidate Solutions at 40° C.

| Candidate Solutions (40° C.) | Storage (Weeks) | | | | | | |
|---|---|---|---|---|---|---|---|
| | 0 | 1 | 2 | 3 | 4 | 14 | 33 |
| Melatonin (ng/ml) | ✓ | ✓ | ✓ | ✓ | ✓ | ✓ | ✓ |
| Osmolality | ✓ | — | — | — | ✓ | — | ✓ |
| pH | ✓ | ✓ | ✓ | ✓ | ✓ | ✓ | ✓ |

Concentrated (×5) candidate solutions 0-9 were stored in climatic chambers at 40° C. and sampled according to Table 7.

TABLE 7

Sampling points for 5x Candidate Solutions

| 5x Cand. Solutions (40° C.) | Storage (Weeks) 12 |
|---|---|
| Melatonin (ng/ml) | ✓ |
| Osmolality | — |
| pH | ✓ |

Analytical Tests and Protocols

The analytical methods used during the study are summarized in Table 8.

TABLE 8

Analytical methods used during the study.

| Determination | Protocol Used |
|---|---|
| Melatonin content | HPLC-FL method for the determination of melatonin in candidate formulations (below) and Melatonin bulk solutions in glass bottle and plastic bag |
| Osmolality | European Pharmacopoeia 2.2.35 - "Osmolality" |
| pH | European Pharmacopoeia 2.2.3 - "Potentiometric determination of pH" |

HPLC-FL Method for the Determination of Melatonin in Candidate Formulations and Melatonin Bulk Solutions in Glass Bottle and Plastic Bag An HPLC-FL method was developed to provide a means of determining metatonin concentrations in various samples.

The chromatographic conditions developed are as follows:

(FM) mobile phase: Acetonitrile:water $H_3PO_4$ 0.25% (20:80)

Loop: 50 µl

Detector: excitation 224 nm; emission: 348 nm

Flow: 1.5 ml/min

Acquisition Duration: 15 min

Column Temp.: Room Temperature

Column: Phenomenex Luna C18 150×4.6 mm, 5 µm

Analytical samples were prepared as follows:

Melatonin Stock solution 1 mg/ml (SM):

Weigh accurately 100 mg of melatonin standards, bring up to volume with Acetonitrile in a 100 ml volumetric flask.

Melatonin Working 20 ng/ml Standard (WS):

Withdraw 1 ml SM with a calibrated glass pipette, bring up to 500 ml with FM in a graduated flask. With a calibrated glass pipette withdraw 1 ml from the resulting solution and bring it to 100 ml in a graduated flask.

Inject the sample as is.

System suitability was tested by confirming that the following conditions are met:

The chromatographic profile of FM solution has no spikes at the retention time of melatonin;

The relative Standard deviation of 3 injections of WS solution is 2.5%.

The content of melatonin in a sample was calculated using the following formula:

$$\text{Melatonin (ng/mL)} = (Ac \cdot Cs)/As$$

where:

Cs=concentration of the WS solution in ng/ml
Ac=Area of the sample
As=Area of the standard Cs is calculated as follows:

$$Cs = (m \cdot T \cdot 100)/D$$

where:

m=weight of SM melatonin solution in mg;
T=% purity of melatonin in % according to the melatonin's certificate of analysis;
D=dilution factor of SM solution.

The analytical method has been verified in terms of specificity compared to impurities and degradation products of melatonin and compared to excipients used in the preparation of formulations. The linearity, precision, accuracy, have been verified and limit of detection and quantification have also been estimated.

Example 0—Preparation of Candidate 0

Candidate 0 was prepared to the following formula:

| Substance | Quantity |
|---|---|
| Melatonin | 20 ng/ml |
| Phosphate buffer | 10 mM |
| Water for Injection (WFI) | q.b. |

The following primary containers were utilised during the preparation of Candidate 0:

| Materials |
|---|
| Sterile vials (37 cm × 22 cm × 7.5 cm) |
| Sterile rubber stoppers |
| Aluminium seal ring and flip-off caps |

Candidate 0 was then prepared in accordance with the following procedure:

1. Preparations of Solutions:
   a. Phosphate buffer (10×PB) 0.1M, pH7.5-7.8 is produced by: weighing 27.6 g of sodium phosphate dibasic dodecahidrate, and 3.5 g of sodium phosphate monobasic bihydrate; and transferring to a 1000 ml flask before adding about 700 ml of the WFI using a 1000 ml graduated cylinder. The mixture is then placed under magnetic stirring until completely dissolution. The pH of the solution is brought to a value that falls between 7.5-7.8 with ortho-phosphoric acid or sodium hydroxide (diluted at an appropriate concentration) before bringing to the required volume with WFI. The solution is then rechecked to ensure that the pH falls between 7.5-7.8 and, if required, eventually adjusted with ortho-phosphoric acid or Sodium hydroxide (diluted at an appropriate concentration).

b. Melatonin solution (4 μg/ml) is produced by: weighing 100.0 mg of Melatonin in a 1000 ml volumetric flask, and adding about 750 ml of WFI before placing under magnetic stirring for at least 30 minutes. After complete dissolution has occurred, the volume is brought upto the required level with WFI (Sol. A). 10 ml of Sol. A is withdrawn using a calibrated pipette, transferred to a 50 ml volumetric flask and brought upto the required volume with WFI (Sol. B). 10 ml of Sol. B is withdrawn using a calibrated pipette, transferred to a 50 ml volumetric flask and again brought to the required volume with WFI Sol. C at 4 μg/ml. The final solution is kept away from light before use.

2. Compounding
a. About 500 ml of WFI is added to a 1000 ml volumetric flask.
b. 100 ml of the Phosphate Buffer (10×PB) is added to the 1000 mL volumetric flask.
c. 5 ml of the Melatonin Solution 4 μg/ml is added and the mixture stirred for 5 minutes.
d. The pH of the mixture is then brought to a pH between 7.5 and 7.8 with ortho-phosphoric acid or sodium hydroxide (diluted at an appropriate concentration).
e. The volume is then brought up to the required volume with WFI and eventually the pH is adjusted to 7.5-7.8 with ortho-phosphoric acid or sodium hydroxide (diluted at an appropriate concentration).
f. About 10 ml of the solution is withdrawn and placed under HPLC analysis for the determination of melatonin content.

3. Sterile Filtration:
a. The obtained mixture is then sterilized via filtration, operating under the laminar flow hood, with Millipak 20 filter (Millipore, code: MPGL02GH2) before transferring the filtrate to a 1000 ml bottle with screw-on lid.
b. Before filtration, let flow from the filter about 1000 ml of the 0.1M Phosphate Buffer diluted at 1:10;
c. The Millipak 20 filter must be pre-flowed before using with 100 ml of formulation. Remove the solution filtered as is.
d. Withdraw about 10 ml of solution and place under HPLC analysis for the determination of Melatonin content.

The resulting sterile solution is distributed into glass vials by: operating under the laminar flow hood, assemble the dispenser, previously sterilized, in the bottle which holds the solution; set the dispensing volume at 2.5 ml on the dispenser; fill, close 200 vials with the solution; and finally measure the osmolality of the solution.

Example 1—Preparation of Candidate 1

Candidate 1 was prepared to the following formula:

| Substance | Quantity |
| --- | --- |
| L-Arginine HCL | 0.1 mg/ml |
| Melatonin | 20 ng/ml |
| Polysorbate 20 | 0.05 mg/ml |
| Phosphate buffer | 10 mM |
| Sodium chloride | 9 mg/ml |
| Water for Injection (WFI) | q.b. |

Candidate 1 was then prepared in accordance with the following procedure, using the same equipment as detailed in Example 0:

1. PREPARATIONS OF SOLUTIONS:
a. Saline Phosphate buffer (10×PBS) is prepared in the same manner as the phosphate buffer in Example 0, except that 90.0 g sodium chloride was additionally mixed into the buffer to produce a saline phosphate buffer.
b. Melatonin solutions (4 μg/ml) is prepared in the same manner as the melatonin solutions set forth in Example 0.
c. Polysorbate 20 (10 mg/ml) is prepared by weighing 500.0 mg of Polysorbate 20 in a 50 ml volumetric flask, and bring up to volume with WFI.

2. COMPOUNDING: Mixtures were prepared in the same manner as per Example 0, except that in addition:
a. 100.0 mg of L-Arginine HCl is added to the 1000 ml volumetric flask and dissolved under magnetic stirring in the 100 mL saline phosphate buffer (10×PBS) and 500 mL of WFI; and
b. Polysorbate 20 solution (10 mg/ml) is added using a 5 ml calibrated pipette whilst the mixture is still stirring;
c. before finally adding the Melatonin Solution 4 μg/ml and continuing the procedure as per Example 0.

3. STERILE FILTRATION: performed as per Example 0.

The resulting sterile solution is distributed into glass vials by: operating under the laminar flow hood, assemble the dispenser, previously sterilized, in the bottle which holds the solution; set the dispensing volume at 2.5 ml on the dispenser; fill, close 200 vials with the solution; and finally measure the osmolality of the solution.

Example 2—Preparation of Candidate 2

Candidate 2 was prepared to the following formula:

| Substance | Quantity |
| --- | --- |
| L-Arginine HCL | 0.1 mg/ml |
| L-methionine | 0.01 mg/ml |
| Melatonin | 20 ng/ml |
| Polysorbate 20 | 0.05 mg/ml |
| Phosphate buffer | 10 mM |
| Sodium chloride | 9 mg/ml |
| Water for Injection (WFI) | q.b. |

Candidate 2 was then prepared in accordance with the following procedure, using the same equipment as detailed in Example 0:

1. PREPARATIONS OF SOLUTIONS:
a. Saline Phosphate buffer (10×PBS) is prepared in the same manner as the phosphate buffer in Example 1.
b. Melatonin solutions (4 μg/ml) is prepared in the same manner as the melatonin solutions set forth in Example 0.
c. Polysorbate 20 (10 mg/ml) is prepared in the same manner as the polysorbate 20 in Example 1.

d. L-Methionine (0.1 mg/ml) solution is prepared by weighing 100.0 mg of L-Methionine in a 1000 ml volumetric flask, and bringing to volume with WFI water.
2. COMPOUNDING: Mixtures were prepared in the same manner as per Example 1, except that in addition:
   a. 100.0 ml of L-Methionin (0.1 mg/ml) is added along with the saline phosphate buffer and WFI to dissolve, under magnetic stirring, the L-arginine.HCl.
3. STERILE FILTRATION: performed as per Example 1.

The resulting sterile solution is distributed into glass vials by: operating under the laminar flow hood, assemble the dispenser, previously sterilized, in the bottle which holds the solution; set the dispensing volume at 2.5 ml on the dispenser; fill, close 200 vials with the solution; and finally measure the osmolality of the solution.

Example 3—Preparation of Candidate 3

Candidate 3 was prepared to the following formula:

| Substance | Quantity |
| --- | --- |
| L-Arginine HCL | 0.1 mg/ml |
| Melatonin | 20 ng/ml |
| Polysorbate 20 | 0.05 mg/ml |
| Hystidinate buffer | 10 mM |
| Sodium chloride | 9 mg/ml |
| Water for Injection (WFI) | q.b. |

Candidate 3 was then prepared in accordance with the following procedure, using the same equipment as detailed in Example 0:
1. PREPARATIONS OF SOLUTIONS:
   a. Melatonin solutions (4 μg/ml) is prepared in the same manner as the melatonin solutions set forth in Example 0.
   b. Polysorbate 20 (10 mg/ml) is prepared in the same manner as the polysorbate 20 in Example.
2. COMPOUNDING:
   a. Weigh 1.555 g of L-Histidine in a container and transfer it in a 1000 ml volumetric flask, rinsing the container with WFI water and adding the washing water to the same flask;
   b. Weigh 9 g of NaCl in a container and transfer it in the 1000 ml volumetric flask at point 6.2.a), rinsing the container with WFI water and adding the washing water to the same flask;
   c. Weigh 100.0 mg of L-Arginine HCl in a container and transfer it in a 1000 ml volumetric flask at point 6.2.a), rinsing the container with WFI water and adding the washing water to the same flask;
   d. Add about 500 ml of WFI and place under magnetic stirring until completely dissolved;
   e. Keeping it under stirring conditions, add 5 ml of Polysorbate 20 solution (10 mg/ml) by using a calibrated pipette;
   f. Add 5 ml Melatonin 4 μg/ml solution and continue the stirring for 5 minutes;
   g. Bring to a pH 7.5-7.8 with hydrochloric acid or Sodium hydroxide (diluted at an appropriate concentration);
   h. Bring to volume with WFI and eventually adjust the pH to 7.5-7.8 with hydrochloric acid or Sodium hydroxide (diluted at an appropriate concentration).

Withdraw about 10 ml of the solution and place under HPLC analysis for the determination of title in Melatonin.
3. STERILE FILTRATION: performed as per Example 2.

The resulting sterile solution is distributed into glass vials by: operating under the laminar flow hood, assemble the dispenser, previously sterilized, in the bottle which holds the solution; set the dispensing volume at 2.5 ml on the dispenser; fill, close 200 vials with the solution; and finally measure the osmolality of the solution.

Example 4—Preparation of Candidate 4

Candidate 4 was prepared to the following formula:

| Substance | Quantity |
| --- | --- |
| L-Arginine HCL | 0.1 mg/ml |
| L-methionine | 13 ng/ml |
| Melatonin | 20 ng/ml |
| Polysorbate 20 | 0.05 mg/ml |
| Phosphate buffer | 10 mM |
| Sodium chloride | 9 mg/ml |
| Water for Injection (WFI) | q.b. |

Candidate 4 was then prepared in accordance with the following procedure, using the same equipment as detailed in Example 0:
1. PREPARATIONS OF SOLUTIONS:
   a. Saline Phosphate buffer (10×PBS) is prepared in the same manner as the phosphate buffer in Example 1.
   b. Melatonin solutions (4 μg/ml) is prepared in the same manner as the melatonin solutions set forth in Example 0.
   c. Polysorbate 20 (10 mg/ml) is prepared in the same manner as the polysorbate 20 in Example 1.
   d. L-Methionine (2.6 μg/ml) solution is prepared by first weighing 130.0 mg of L-Methionine in a 1000 ml volumetric flask, and bring to volume with WFI water. Then withdraw 10 ml of L-Methionine 0.13 mg/ml in a 50 ml volumetric flask, and bring to volume with WFI water. Finally, withdraw 5 ml of L-Methionine 26 μg/ml in a 50 ml volumetric flask, and bring to volume with WFI water.
2. COMPOUNDING:
   a. Weigh 100.0 mg of L-Arginine HCl and transfer it in a 1000 ml volumetric flask;
   b. Add 5 ml of L-Methionine 2.6 μg/ml and transfer it in the flask;
   c. Add, using a volumetric flask, 100 ml of Saline Phosphate Buffer (10×PBS);
   d. Add about 500 ml of WFI and place under magnetic stirring until completely dissolved;
   e. While kept under stirring, add, using a 5 ml calibrated pipette, the Polysorbate 20 solution (10 mg/ml);
   f. Add 5 ml of the Melatonin 4 μg/ml solution and continue the stirring for 5 minutes;
   g. Bring to a pH 7.5-7.8 with ortho-phosphoric acid or Sodium hydroxide (diluted at an appropriate concentration);
   h. Bring to volume with WFI and eventually adjust the pH to 7.5-7.8 with ortho-phosphoric acid or Sodium hydroxide (diluted at an appropriate concentration
   i. Withdraw about 10 ml of the solution and place under HPLC analysis for the determination of title in Melatonin.

3. STERILE FILTRATION: performed as per Example 1 with the exception that Nitrogen gas was flushed for 30 minutes to displace oxygen from solution, before filtration The resulting sterile solution is distributed into glass vials by: operating under the laminar flow hood, assemble the dispenser, previously sterilized, in the bottle which holds the solution; set the dispensing volume at 2.5 ml on the dispenser; fill, close 200 vials with the solution; and finally measure the osmolality of the solution.

Example 5—Preparation of Candidate 5

Candidate 5 was prepared to the following formula:

| Substance | Quantity |
| --- | --- |
| L-Arginine HCL | 0.1 mg/ml |
| L-Cystein HCl × H2O | 0.01 mg/ml |
| Melatonin | 20 ng/ml |
| Polysorbate 20 | 0.05 mg/ml |
| Phosphate buffer | 10 mM |
| Sodium chloride | 9 mg/ml |
| Water for Injection (WFI) | q.b. |

Candidate 5 was then prepared in accordance with the following procedure, using the same equipment as detailed in Example 0:
1. PREPARATIONS OF SOLUTIONS:
    a. Saline Phosphate buffer (10×PBS) is prepared in the same manner as the phosphate buffer in Example 1.
    b. Melatonin solutions (4 µg/ml) is prepared in the same manner as the melatonin solutions set forth in Example 0.
    c. Polysorbate 20 (10 mg/ml) is prepared in the same manner as the polysorbate 20 in Example 1.
    d. L-Cystein HClxH2O (0.1 mg/ml) is prepared by weighing 100.0 mg of L-cystein HClxH2O in a 1000 ml volumetric flask, and bringing to volume with WFI water.
2. COMPOUNDING: The mixture was prepared as per Example 4, except that the addition of 5 ml of L-Methionine 2.6 µg/ml is replaced by the addition of 100.0 ml of L-cystein HClxH2O 0.1 mg/ml with a 100 ml volumetric flask.
4. STERILE FILTRATION: performed as per Example 1.

The resulting sterile solution is distributed into glass vials by: operating under the laminar flow hood, assemble the dispenser, previously sterilized, in the bottle which holds the solution; set the dispensing volume at 2.5 ml on the dispenser; fill, close 200 vials with the solution; and finally measure the osmolality of the solution.

Example 6—Preparation of Candidate 6

Candidate 6 was prepared to the following formula:

| Substance | Quantity |
| --- | --- |
| L-Arginine HCL | 0.1 mg/ml |
| L-methionine | 0.01 mg/ml |
| Melatonin | 20 ng/ml |
| Propylen glycol | 6 mg/ml |
| Phosphate buffer | 10 mM |
| Sodium chloride | 7 mg/ml |
| Water for Injection (WFI) | q.b. |

Candidate 6 was then prepared in accordance with the following procedure, using the same equipment as detailed in Example 0:
1. PREPARATIONS OF SOLUTIONS:
    a. Phosphate buffer is prepared in the same manner as the phosphate buffer in Example 0.
    b. Melatonin solutions (4 µg/ml) is prepared in the same manner as the melatonin solutions set forth in Example 0.
    c. L-Methionine (0.1 mg/ml) solution is prepared as per Example 2.
2. COMPOUNDING:
    a. Weigh 100.0 mg of L-Arginine HCl and transfer it in a 1000 ml volumetric flask;
    b. Weigh 7 g of NaCl in a container and transfer it in the 1000 ml volumetric flask, rinsing the container with WFI water and adding the washing liquids in the same flask;
    c. Add, using a volumetric flask, 100 ml of Phosphate Buffer (10×PB);
    d. Add 100.0 ml of L-Methionine 0.1 mg/ml with a 100 ml volumetric flask.
    e. Add about 500 ml of WFI and place under magnetic stirring until completely dissolved;
    f. Weigh 6.0 g of Propylen glycol and transfer it in a 1000 ml volumetric flask;
    g. Add 5 ml of the Melatonin 4 µg/ml solution and continue the stirring for 5 minutes;
    h. Bring to a pH 7.5-7.8 with ortho-phosphoric acid or Sodium hydroxide (diluted at an appropriate concentration);
    i. Bring to volume with WFI and eventually adjust the pH to 7.5-7.8 with ortho-phosphoric acid or Sodium hydroxide (diluted at an appropriate concentration
    j. Withdraw about 10 ml of the solution and place under HPLC analysis for the determination of title in Melatonin.
5. STERILE FILTRATION: performed as per Example 1.

The resulting sterile solution is distributed into glass vials by: operating under the laminar flow hood, assemble the dispenser, previously sterilized, in the bottle which holds the solution; set the dispensing volume at 2.5 ml on the dispenser; fill, close 200 vials with the solution; and finally measure the osmolality of the solution.

Example 7—Preparation of Candidate 7

Candidate 7 was prepared to the following formula:

| Substance | Quantity |
| --- | --- |
| L-glycine | 8 mg/ml |
| L-methionine | 0.01 mg/mL |
| Melatonin | 20 ng/ml |
| Phosphate buffer | 10 mM |
| Sodium chloride | 6 mg/ml |
| Water for Injection (WFI) | q.b. |

Candidate 7 was then prepared in accordance with the following procedure, using the same equipment as detailed in Example 0:
1. PREPARATIONS OF SOLUTIONS:
    a. Phosphate buffer is prepared in the same manner as the phosphate buffer in Example 0.
    b. Melatonin solutions (4 µg/ml) is prepared in the same manner as the melatonin solutions set forth in Example 0.

c. L-Methionine (0.1 mg/ml) solution is prepared as per Example 2.
2. PREPARATION OF MIXTURE (MIXING OF SOLUTIONS):
   a. Weigh 8.0 g of L-glycine in a container and transfer it in a 1000 ml volumetric flask, rinsing the container with WFI water and adding the washing liquids in the same flask;
   b. Weigh 6 g of NaCl in a container and transfer it in the 1000 ml volumetric flask, rinsing the container with WFI water and adding the washing liquids in the same flask;
   c. Add 100.0 ml of L-Methionine 0.1 mg/ml with a 100 ml volumetric flask;
   d. Add, using a volumetric flask, 100 ml of the Phosphate Buffer (10×PB);
   e. Add about 500 ml of WFI and place under magnetic stirring until completely dissolved;
   f. Add 5 ml of Melatonin 4 µg/ml solution and continue stirring for 5 minutes;
   g. Bring to a pH 7.5-7.8 with ortho-phosphoric acid or Sodium hydroxide (diluted at an appropriate concentration).
   h. Bring to volume with WFI and eventually adjust the pH to 7.5-7.8 with ortho-phosphoric acid or Sodium hydroxide (diluted at an appropriate concentration).
   i. Withdraw about 10 ml of the solution and place under HPLC analysis for the determination of title in Melatonin.
6. STERILE FILTRATION: performed as per Example 1.

The resulting sterile solution is distributed into glass vials by: operating under the laminar flow hood, assemble the dispenser, previously sterilized, in the bottle which holds the solution; set the dispensing volume at 2.5 ml on the dispenser; fill, close 200 vials with the solution; and finally measure the osmolality of the solution.

Example 8—Preparation of Candidate 8

Candidate 8 was prepared to the following formula:

| Substance | Quantity |
| --- | --- |
| Melatonin | 20 ng/ml |
| Glucose | 20 mg/ml |
| Phosphate buffer | 10 mM |
| Sodium chloride | 6 mg/ml |
| Water for Injection (WFI) | q.b. |

Candidate 8 was then prepared in accordance with the following procedure, using the same equipment as detailed in Example 0:
1. PREPARATIONS OF SOLUTIONS:
   a. Phosphate buffer is prepared in the same manner as the phosphate buffer in Example 0.
   b. Melatonin solutions (4 µg/ml) is prepared in the same manner as the melatonin solutions set forth in Example 0.
2. COMPOUNDING):
   a. Weigh 20.0 g of Glucose in a container and transfer it in a 1000 ml volumetric flask, rinsing the container with WFI water and adding the washing liquids in the same flask;
   b. Weigh 6 g of NaCl in a container and transfer it in the 1000 ml volumetric flask, rinsing the container with WFI water and adding the washing liquids in the same flask;
   c. Add, using a volumetric flask, 100 ml of the Phosphate Buffer (10×PB);
   d. Add about 500 ml of WFI and place under magnetic stirring until completely dissolved;
   e. Add 5 ml of Melatonin 4 µg/ml solution and continue stirring for 5 minutes;
   f. Bring to a pH 7.5-7.8 with ortho-phosphoric acid or Sodium hydroxide (diluted at an appropriate concentration).
   g. Bring to volume with WFI and eventually adjust the pH to 7.5-7.8 with ortho-phosphoric acid or Sodium hydroxide (diluted at an appropriate concentration).
   h. Withdraw about 10 ml of the solution and place under HPLC analysis for the determination of title in Melatonin.
7. STERILE FILTRATION: performed as per Example 1.

The resulting sterile solution is distributed into glass vials by: operating under the laminar flow hood, assemble the dispenser, previously sterilized, in the bottle which holds the solution; set the dispensing volume at 2.5 ml on the dispenser; fill, close 200 vials with the solution; and finally measure the osmolality of the solution.

Example 9—Preparation of Candidate 9

Candidate 9 was prepared to the following formula:

| Substance | Quantity |
| --- | --- |
| Sucrose | 50 mg/ml |
| L-methionine | 0.01 mg/ml |
| Melatonin | 20 ng/ml |
| Polysorbate 20 | 0.05 mg/ml |
| Phosphate buffer | 10 mM |
| Water for Injection (WFI) | q.b. |

Candidate 9 was then prepared in accordance with the following procedure, using the same equipment as detailed in Example 0:
1. PREPARATIONS OF SOLUTIONS:
   a. Phosphate buffer is prepared in the same manner as the phosphate buffer in Example 0.
   b. Melatonin solutions (4 µg/ml) is prepared in the same manner as the melatonin solutions set forth in Example 0.
   c. Polysorbate 20 (10 mg/ml) is prepared in the same manner as the polysorbate 20 in Example 1.
   d. L-Methionine (0.1 mg/ml) solution is prepared in the same manner as in Example 2
2. COMPOUNDING:
   a. Weigh 50.0 g of Sucrose and transfer it in a 1000 ml volumetric flask;
   b. Add, using a volumetric flask, 100 ml of Phosphate Buffer(10×PB);
   c. Add 100.0 ml of L-Methionine 0.1 mg/ml with a 100 ml volumetric flask;
   d. Keeping under stirring conditions, add by using a 5 ml calibrated pipette of Polysorbate 20 solution (10 mg/ml);
   e. Add about 500 ml of WFI and place under magnetic stirring until completely dissolved;
   f. Add 5 ml of Melatonin 4 µg/ml solution and continue stirring for 5 minutes;
   g. Bring to a pH 7.5-7.8 with ortho-phosphoric acid or Sodium hydroxide (diluted at an appropriate concentration);

h. Bring to volume with WFI and eventually adjust the pH to 7.5-7.8 with ortho-phosphoric acid or Sodium hydroxide. (diluted at an appropriate concentration).

i. Withdraw about 10 ml of the solution and place under HPLC analysis for the determination of title in Melatonin.

8. STERILE FILTRATION: performed as per Example 1.

The resulting sterile solution is distributed into glass vials by: operating under the laminar flow hood, assemble the dispenser, previously sterilized, in the bottle which holds the solution; set the dispensing volume at 2.5 ml on the dispenser; fill, close 200 vials with the solution; and finally measure the osmolality of the solution.

Results 1—Analysis of Bulk Solutions Over Time

The aforementioned bulk solutions (bottled and bagged) were analysed over time, in terms of melatonin content, osmolality, and pH. The results are presented in Table 9A and 9B below.

TABLE 9A

Results of Analytical Tests (up to 42 days storage at room temperature) on Bottled Bulk Solution of Melatonin

| | Bulk Solutions (Room Temperature) Storage (Days) | | | | |
|---|---|---|---|---|---|
| | 1 | 3 | 7 | 25 | 42 |
| Melatonin (ng/ml) | 22.3 | 21.6 | 20.8 | 21.1 | 21.7 |
| Osmolality | 309 | 313 | 306 | 315 | 317 |
| pH | — | — | — | — | 7.6 |

TABLE 9B

Results of Analytical Tests (up to 42 days storage at room temperature) on Bulk Solution of Melatonin in plastic bags

| | Bulk Solutions (Room Temperature) Storage (Days) | | | | |
|---|---|---|---|---|---|
| | 1 | 3 | 7 | 25 | 42 |
| Melatonin (ng/ml) | 21.8 | 21.4 | 20.8 | 20.9 | 21.6 |
| Osmolality | 304 | 308 | 315 | 301 | 312 |
| pH | — | — | — | — | 7.6 |

Results 2—Analysis of Concentrated (5×) Candidate Solutions Under Different Storage Conditions Concentrated (5×) candidate solutions 0 to 9 (100 ng/mL melatonin) were analysed (melatonin content and pH) over time under different storage conditions. The results are presented in Table 10A and 10B below.

TABLE 10A

Results of Melatonin Content Tests for Concentrated x5 Candidate 0-9 (after 12 weeks storage at 40° C.)

| 5x Candidate Solutions (40° C.) Melatonin (ng/ml) | Storage (Weeks) 12 |
|---|---|
| Candidate 0 | — |
| Candidate 1 | — |
| Candidate 2 | 94.4 |
| Candidate 3 | 21.8 |
| Candidate 4 | 84.4 |
| Candidate 5 | — |
| Candidate 6 | 97.5 |
| Candidate 7 | — |
| Candidate 8 | 5.0 |
| Candidate 9 | 50.4 |

TABLE 10B

Results of pH Tests for Concentrated x5 Candidate 0-9 (after 12 weeks storage at 40° C.)

| 5x Candidate Solutions (40° C.) pH | Storage (Weeks) 12 |
|---|---|
| Candidate 0 | — |
| Candidate 1 | — |
| Candidate 2 | 7.7 |
| Candidate 3 | 7.7 |
| Candidate 4 | 7.6 |
| Candidate 5 | — |
| Candidate 6 | 7.6 |
| Candidate 7 | — |
| Candidate 8 | 6.8 |
| Candidate 9 | 7.5 |

Results 3—Analysis of Candidate Solutions (20 ng/mL) Under Different Storage Conditions Candidate solutions 0 to 9 (20 ng/mL melatonin) were analysed (melatonin content, pH, osmolality) over time under different storage conditions. The results are presented in Tables 11A-C, 12A-C, and 13A-C.

TABLE 11A

Results of Melatonin Content Tests for Candidate 0-9 (after 0, 20, and 33 weeks storage at 25° C.)

| Candidate Solutions (25° C.) Melatonin (ng/ml) | Unfiltered Sample | Storage (Weeks) | | |
|---|---|---|---|---|
| | | 0 | 20 | 33 |
| Candidate 0 | 21.7 | 21.0 | 17.9 | — |
| Candidate 1 | 21.5 | 20.9 | 16.1 | — |
| Candidate 2 | 21.3 | 21.1 | 20.9 | 20.5 |
| Candidate 3 | 22.8 | 23.4 | 20.9 | — |
| Candidate 4 | 22.2 | 21.6 | 20.6 | 19.4 |
| Candidate 5 | 20.3 | 21.4 | 15.2 | — |
| Candidate 6 | 21.7 | 20.9 | 20.6 | 20.0 |
| Candidate 7 | 21.8 | 21.1 | 19.7 | 18.9 |
| Candidate 8 | 20.4 | 20.8 | — | — |
| Candidate 9 | 21.3 | 20.7 | 19.2 | 17.9 |

TABLE 11B

Results of pH Tests for Candidate 0-9 (after 0, 20, and 33 weeks storage at 25° C.)

| Candidate Solutions (25° C.) pH | Storage (Weeks) | | |
|---|---|---|---|
| | 0 | 20 | 33 |
| Candidate 0 | 7.6 | 7.6 | — |
| Candidate 1 | 7.6 | 7.5 | — |
| Candidate 2 | 7.7 | 7.6 | 7.6 |
| Candidate 3 | 7.7 | 7.6 | — |
| Candidate 4 | 7.7 | 7.6 | 7.6 |
| Candidate 5 | 7.7 | 7.6 | — |
| Candidate 6 | 7.8 | 7.7 | 7.8 |
| Candidate 7 | 7.6 | 7.5 | 7.6 |
| Candidate 8 | 7.6 | — | — |
| Candidate 9 | 7.7 | 7.6 | 7.7 |

TABLE 12B

Results of pH Tests for Candidate 0-9 (after 0-4, 14, and 33 weeks storage at 40° C.)

| Candidate Solutions (40° C.) pH | Storage (Weeks) | | | | | | |
|---|---|---|---|---|---|---|---|
| | 0 | 1 | 2 | 3 | 4 | 14 | 33 |
| Candidate 0 | 7.6 | 7.6 | — | 7.6 | 7.6 | — | |
| Candidate 1 | 7.6 | 7.6 | — | 7.5 | 7.5 | — | |
| Candidate 2 | 7.7 | 7.6 | | 7.6 | 7.6 | 7.6 | 7.6 |
| Candidate 3 | 7.7 | 7.6 | — | 7.6 | 7.6 | 7.3 | |
| Candidate 4 | 7.7 | 7.7 | — | 7.6 | 7.6 | 7.6 | |
| Candidate 5 | 7.7 | 7.6 | — | 7.6 | 7.6 | | |
| Candidate 6 | 7.8 | 7.8 | | 7.8 | 7.8 | 7.7 | 7.7 |
| Candidate 7 | 7.6 | 7.6 | | 7.5 | 7.5 | | |
| Candidate 8 | 7.6 | 7.5 | 7.2 | 7.2 | 7.0 | | |
| Candidate 9 | 7.7 | 7.6 | | 7.6 | 7.6 | 7.6 | |

TABLE 11C

Results of Osmolality Tests for Candidate 0-9 (after 0, 20, and 33 weeks storage at 25° C.)

| Candidate Solutions (25° C.) Osmolality (mOsm/Kg) | Storage (Weeks) | | |
|---|---|---|---|
| | 0 | 20 | 33 |
| Candidate 0 | — | — | — |
| Candidate 1 | 308 | 293 | — |
| Candidate 2 | 303 | 307 | 310 |
| Candidate 3 | 299 | 302 | — |
| Candidate 4 | 296 | 316 | 310 |
| Candidate 5 | 309 | 309 | — |
| Candidate 6 | 329 | 330 | 339 |
| Candidate 7 | 315 | 316 | 320 |
| Candidate 8 | 322 | — | — |
| Candidate 9 | 179 | 182 | 188 |

TABLE 12C

Results of Osmolality Tests for Candidate 0-9 (after 0, 4, and 33 weeks storage at 40° C.)

| Candidate Solutions (40° C.) Osmolality (mOsm/Kg) | Storage (Weeks) | | |
|---|---|---|---|
| | 0 | 4 | 33 |
| Candidate 0 | — | — | — |
| Candidate 1 | 308 | 316 | — |
| Candidate 2 | 303 | 309 | 313 |
| Candidate 3 | 299 | 301 | — |
| Candidate 4 | 296 | 315 | — |
| Candidate 5 | 309 | 318 | — |
| Candidate 6 | 329 | 337 | 341 |
| Candidate 7 | 315 | 325 | — |
| Candidate 8 | 322 | 328 | — |
| Candidate 9 | 179 | 187 | — |

TABLE 12A

Results of Melatonin Content Tests for Candidate 0-9 (after 0-4, 14, and 33 weeks storage at 40° C.)

| Candidate Solutions (40° C.) Melatonin (ng/ml) | Storage (Weeks) | | | | | | |
|---|---|---|---|---|---|---|---|
| | 0 | 1 | 2 | 3 | 4 | 14 | 33 |
| Candidate 0 | 21.0 | 21.0 | — | 20.9 | 20.4 | | |
| Candidate 1 | 20.9 | 21.2 | — | 17.6 | 17.9 | | |
| Candidate 2 | 21.1 | 21.6 | — | 22.1 | 21.1 | 20.8 | 20.4 |
| Candidate 3 | 23.4 | 23.5 | — | 23.7 | 22.7 | 5.7 | |
| Candidate 4 | 21.6 | 21.7 | — | 22.2 | 21.6 | 19.7 | |
| Candidate 5 | 21.4 | 21.5 | — | 21.6 | 20.3 | | |
| Candidate 6 | 20.9 | 20.8 | | 21.4 | 21.0 | 20.3 | 17.0 |
| Candidate 7 | 21.1 | 20.1 | | 20.9 | 20.1 | | |
| Candidate 8 | 20.8 | 14.3 | 11.1 | 8.7 | 6.8 | | |
| Candidate 9 | 20.7 | 19.9 | | 20.5 | 20.5 | 13.6 | |

TABLE 13A

Results of Melatonin Content Tests for Candidate 0-9 (after 0 and 33 weeks storage at 2-8° C.)

| Candidate Solutions (2-8° C.) Melatonin (ng/ml) | Storage (Weeks) | |
|---|---|---|
| | 0 | 33 |
| Candidate 0 | 21.0 | — |
| Candidate 1 | 20.9 | — |
| Candidate 2 | 21.1 | 21.1 |
| Candidate 3 | 23.4 | |
| Candidate 4 | 21.6 | |
| Candidate 5 | 21.4 | |
| Candidate 6 | 20.9 | 20.1 |
| Candidate 7 | 21.1 | |
| Candidate 8 | 20.8 | |
| Candidate 9 | 20.7 | |

TABLE 13B

Results of pH Tests for Candidate 0-9 (after
0 and 33 weeks storage at 2-8° C.)

| Candidate Solutions (2-8° C.) pH | Storage (Weeks) | |
| --- | --- | --- |
| | 0 | 33 |
| Candidate 0 | 7.6 | |
| Candidate 1 | 7.6 | |
| Candidate 2 | 7.7 | 7.6 |
| Candidate 3 | 7.7 | |
| Candidate 4 | 7.7 | |
| Candidate 5 | 7.7 | |
| Candidate 6 | 7.8 | 7.8 |
| Candidate 7 | 7.6 | |
| Candidate 8 | 7.6 | |
| Candidate 9 | 7.7 | |

TABLE 13C

Results of Osmolality Tests for Candidate 0-9
(after 0 and 33 weeks storage at 2-8° C.)

| Candidate Solutions (2-8° C.) Osmolality (mOsm/Kg) | Storage (Weeks) | |
| --- | --- | --- |
| | 0 | 33 |
| Candidate 0 | | |
| Candidate 1 | 308 | |
| Candidate 2 | 303 | 312 |
| Candidate 3 | 299 | |
| Candidate 4 | 296 | |
| Candidate 5 | 309 | |
| Candidate 6 | 329 | 343 |
| Candidate 7 | 315 | |
| Candidate 8 | 322 | |
| Candidate 9 | 179 | |

CONCLUSIONS

The results demonstrate the impressive storage stability of formulations of the invention, all of which contain melatonin (or one of its analogs) which is notoriously unstable in solution. Particularly advantageous formulations are those comprising a sulphur-containing amino acid, especially methionine, especially where methionine is present in combination with arginine.

The invention claimed is:

1. A topical liquid composition for intrauterine washing, the composition comprising:
   a. 2-200 ng/ml melatonin (N-acetyl-5-methoxytryptamine) or an analog thereof, or a pharmaceutically acceptable salt or solvate thereof;
   b. 0.01-100 mM phosphate buffer system;
   c. $1\times10^{-6}$-5 mg/ml methionine or cysteine;
   d. 0.0008-8 mg/ml arginine;
   e. 1-100 mg/ml sodium chloride;
   f. a surfactant selected from 0.001-10 mg/ml polysorbate 20 and 0.1-100 mg/ml propylene glycol; and
   g. water,
   wherein the pH of the composition is pH 7-8.5, and the composition has an osmolality of 250-350 mOsm/kg.

2. The topical liquid composition as claimed in claim 1, wherein the amino acid in c. is methionine.

3. The topical liquid composition as claimed in claim 1, wherein the surfactant is polysorbate 20.

4. The topical liquid composition as claimed in claim 1, wherein the composition is free of any protein or protein compounds, or else comprises no more than 0.1 wt % of any protein or protein compounds.

5. The topical liquid composition as claimed in claim 1, wherein the composition is free of further amino acids other than those stipulated or else comprise no more than 0.1 mM of any individual further amino acid.

6. The topical liquid composition as claimed in claim 1, wherein the composition has an osmolality of 280-330 mOsm/kg.

7. The topical liquid composition as claimed in claim 1, wherein the composition has a pH between 7.6 and 7.8.

8. The topical liquid composition as claimed in claim 1, wherein the composition comprises:
   a. 15-25 ng/mL melatonin (N-acetyl-5-methoxytryptamine) or an analog thereof, or a pharmaceutically acceptable salt or solvate thereof; and
   b. 5-15 mM phosphate buffer system;
   c. 0.005-0.015 mg/mL methionine;
   d. 0.04-0.4 mg/mL arginine;
   e. 5-12 mg/mL sodium chloride;
   f. 0.025-0.075 mg/mL polysorbate 20;
   g. water (as the remaining balance by weight);
   wherein the pH of the composition is pH 7.6-7.8, and the composition has an osmolality of 295-320 mOsm/kg.

9. A package or medical device, comprising a sterile container pre-filled or configured for filling with a topical liquid composition as claimed in claim 1.

10. A method for inhibiting and/or preventing embryonic implantation failure during assisted reproduction treatment comprising administering to a patient in need thereof a topical liquid composition as claimed in claim 1.

11. The topical liquid composition as claimed in claim 2, wherein the concentration of methione is from 13 ng/ml to 0.01 mg/ml.

12. The topical liquid composition as claimed in claim 1, wherein the composition comprises:
   a. 15-25 ng/ml melatonin (N-acetyl-5-methoxytryptamine) or an analog thereof, or a pharmaceutically acceptable salt or solvate thereof;
   b. 5-15 mM phosphate buffer system;
   c. 0.005-0.015 mg/ml methionine or cysteine;
   d. 0.04-0.4 mg/ml arginine;
   e. 5-12 mg/ml sodium chloride;
   f. a surfactant selected from 0.025-0.075 mg/ml polysorbate 20 and 4-8 mg/ml propylene glycol; and
   g. water,
   wherein the pH of the composition is pH 7.6-7.8, and the composition has an osmolality of 295-315 mOsm/kg.

13. The topical liquid composition as claimed in claim 8, wherein the composition comprises:
   a. 20 ng/ml melatonin (N-acetyl-5-methoxytryptamine) or an analog thereof, or a pharmaceutically acceptable salt or solvate thereof;
   b. 10 mM phosphate buffer system;
   c. 0.01 mg/ml methionine;
   d. 0.1 mg/ml arginine;
   e. 9 mg/ml sodium chloride;
   f. 0.05 mg/ml polysorbate 20; and
   g. water,
   wherein the pH of the composition is pH 7.6-7.8, and the composition has an osmolality of 295-320 mOsm/kg.

14. The topical liquid composition as claimed in claim 1, wherein the composition comprises:

a. 20 ng/ml melatonin (N-acetyl-5-methoxytryptamine) or an analog thereof, or a pharmaceutically acceptable salt or solvate thereof;
b. 10 mM phosphate buffer system;
c. 0.01 mg/ml methionine;
d. 0.1 mg/ml arginine;
e. 7 mg/ml sodium chloride;
f. 6 mg/ml propylene glycol; and
g. water, wherein the pH of the composition is pH 7.6-7.8, and the composition has an osmolality of 295-320 mOsm/kg.

15. The topic liquid composition as claimed in claim 11, wherein the composition comprises:
a. 20 ng/ml melatonin (N-acetyl-5-methoxytryptamine) or an analog thereof, or a pharmaceutically acceptable salt or solvate thereof;
b. 10 mM phosphate buffer system;
c. 13 ng/ml methionine;
d. 0.1 mg/ml arginine;
e. 9 mg/ml sodium chloride;
f. 0.05 mg/ml polysorbate 20; and
g. water, wherein the pH of the composition is pH 7.6-7.8, and the composition has an osmolality of 295-320 mOsm/kg.

* * * * *